(12) United States Patent
Thomas

(10) Patent No.: US 6,587,792 B1
(45) Date of Patent: Jul. 1, 2003

(54) NUCLEAR PACKING EFFICIENCY

(76) Inventor: Richard A. Thomas, 7620 SW., 147 Ct., Miami, FL (US) 33193

( * ) Notice: Subject to any disclaimer, the term of this patent is extended or adjusted under 35 U.S.C. 154(b) by 0 days.

(21) Appl. No.: 09/481,210

(22) Filed: Jan. 11, 2000

(51) Int. Cl.[7] .......................... G01N 31/00; G01N 1/30; G01N 27/00; C12Q 1/68; G01R 27/00

(52) U.S. Cl. .............................. 702/26; 435/6; 435/4; 435/5; 435/40.5; 324/71.4; 324/600

(58) Field of Search ........................ 435/6, 4, 5, 40.5; 324/71.4, 600; 702/26

(56) References Cited

U.S. PATENT DOCUMENTS

| 4,298,836 A | 11/1981 | Groves et al. ............... 324/71 |
| 4,818,103 A | 4/1989 | Thomas et al. ............... 356/72 |
| 6,228,652 B1 | 5/2001 | Rodriguez et al. | |

OTHER PUBLICATIONS

Steinkamp et al., "Improved multilaser/ multiparameter flow cytometer for analysis and sorting of cells and particles", Rev. Soi. Instrum. vol. 62 No. 11, Nov. 1991, pp. 2751–2764.*

Aaltomaa et al., "The Significance of Nuclear Morphometric Variables as Prognostic Predictors in Breast Cancer," *Anticancer Res.*, 11:1663–1670 (1991).

Allison et al., "Computerized Measurement of the DNA Content, Areas, and Autoradiographic Grains of the Same Nuclei: Demonstration that Lightly ($^3$H)Thymidine–labeled Bone Marrow Cells are Predominantly in G0/G1 and G2," *J. Histochem. Cytochem.*, 32:1197–1203 (1984).

Bauer et al., "Consensus Review of the Clinical Utility of DNA Flow Cytometry in Colorectal Cancer," *Cytometry*, 14:486–491 (1993).

Bjelkenkrantz, "An Evaluation of Feulgen–Acriflavine–$SO_2$ and Hoechst 33258 for DNA Cytofluorometry in Tumour Pathology," *Histochemistry*, 79:177–191 (1983).

Cohn et al., "Nuclear and Nuleolar Protein During the Cell Cycle in Differentiating *Pisum sativum* Vascular Tissue," *Histochemistry*, 79:353–364 (1983).

Darzynkiewicz et al., "Accessibility of DNA In Situ to Various Fluorochromes: Relationship to Chromatin Changes During Erythroid Differentiation of Friend Leukemia Cells," *Cytometry*, 5:355–363 (1984).

Grover et al., "Electrical Sizing of Particles In Suspensions I Theory," *Biophysical J.*, 9:1398–1414 (1969).

G undersen and Jensen, "The Efficiency of Systematic Sampling In Stereology and Its Predictions," *J. Microscopy*, 147:229–263 (1987).

Hedley et al., "Consensus Review of the Clinical Utility of DNA Cytometry in Carninoma of the Breast," *Cytometry*, 14:482–485 (1993).

Hubert and Bourgeois, "The Nuclear Sekeleton and the spatial arrangement of chromosomes in the interphase nucleus of vertebrate somatic cells," *Hum. Genet.*, 74:1–15 (1986).

(List continued on next page.)

*Primary Examiner*—Mary K. Zeman
*Assistant Examiner*—Lori A Clow
(74) *Attorney, Agent, or Firm*—Campbell & Flores LLP

(57) ABSTRACT

Methods and devices for determining the nuclear packing efficiency (NPE) of a cell nucleus and other biological particles. An NPE can be determined by correlating at least one biochemical component, such as DNA content, to nuclear volume using a variety of mathematical techniques. Flow cytometry is particularly useful for measuring nuclear volume in terms of the electronic nuclear volume (ENV). The NPE can then be used to characterize individual cells and cell populations in terms of species and tissue source, sexing, stage of the cell division cycle, differentiation and apoptosis, as well as differentiating among benign, malignant and metastatic states to diagnose cancer.

25 Claims, 24 Drawing Sheets

OTHER PUBLICATIONS

Hughes and Cohen, "Nuclear Matrix Proteins and Their Protential Applications to Diagnostic Pathology," *Am. J. Clin. Pathol.*, 111:267–274 (1999).

Irinopoulou et al., "Application of Confocal Scanning Laser Microscopy to 3–D DNA Image Cytometry of Prostatic Lesions," Analytical and Quantitative Cytology and Histology, 20:351–357 (1998).

Irinopoulou et al., "3–D DNA Image Cytometry by Confocal Scanning Laser Microscopy in thick tissue blocks of Prostatic Lesions," *Cytometry*, 1:27 (2):99–105 (1997).

Johnson et al., "Nuclear Size of G1/S Transition Cells Measured by Flow Cytometry," *Exp. Cell Res.*, 134:201–205 (1981).

Krishan, "Rapid Flow Cytofluorometric Analysis of Mammalian Cell Cycle by Propidium Iodide Staining," *J. Cell Biol.*, 66:188–193 (1975).

Leary et al., "Laser Flow Cytometric Light Scatter and Fluorescence Pulse Width and Pulse Rise–Time Sizing of Mammalian Cells," *J. Histochem. Cytochem.*, 27:315–320 (1979).

Lindberg, "Nuclear DNA Ploidy in Mammary Carcinomas; Using Nuclear Size as Co–parameter Reveals More Complex Patterns," *Anal. Cellular Pathol.*, 4:389–394 (1992).

Mullaney et al., "Pulse–Height Light–Scatter Distributions Using Flow–Systems Instrumentation," *J. Histochem. Cytochem.*, 24:289–304 (1976).

Ormerod, *Flow Cytometry*, 2d. Ed., BIOS Scientific Publishers Limited, 1999.

Piwnicka et al., "RNA and DNA Content of Isolated Cell Nuclei Measured by Multiparamater Flow Cycometry," *Cytometry*, 3:269–275 (1983).

Roti Roti et al., "Cell–Cycle Position and Nuclear Protein Content," *Cytometry*, 3:91–96 (1982).

Schieck et al., "Dry Mass, DNA and non–histone protien determinations in lung cancer cells," *Histochemical J.*, 19:504–508 (1987).

Shankey et al., "Guidelines for implementation of clinical DNA cytometry," *Cytometry*, 14:472–477 (1993).

Sharpless et al., Flow Cytofluorimetry: Discrimination Between Single Cells and Cell Aggregates by Direct Size Measurements, *Acta Cytol.*, 19:577–581 (1975).

Staiano–Coico et al., "RNA and DNA Content of Isolated Nuclei from Bladder Irrigation Specimens as Measured by Flow Cytometry," *Analytical and Quantitative Cytology*, 6:24–29 (1984).

Stal and Hatschek, "A Rapid System for Static Cytofluorometry Enabling the Simultaneous Determination of Nuclear Size and DNA Content," *Path. Res. Pract.*, 183:329–335 (1988).

Teodori et al., "DNA/Protein Flow Cytometry as a Predictive Marker of Malignancy in Dysplasia–Free Barrett's Esophagus: Thirteen–Year Follow–up Study on a Cohort of Patients," *Cytometry*, 34:257–263 (1998).

Teodori et al., "Cellular Hetergeneity of DNA/Total–Protein Content in Human Lung Tumors, as Determined by Flow Cytometry," *Int. J. Cancer*, 50:845–853 (1992).

Wheeless et al., "Consensus Review of the Clinical Utility of DNA Cytometry in Bladder Cancer," *Cytometry*, 14:478–481 (1993).

Yen and Pardee, "Role of Nuclear Size in Cell Growth Initiation," *Science*, 22:204:1315–1317 (1979).

Schuette et al., "Design of Flow Chamber with Electronic Cell Volume Capability and Light Detection Optics for Multilaser Flow Cytometry," *Cytometry*, 5:652–656 (1984).

Steinkamp et al., "Improved Multilaser/Multiparameter Flow Cytometer for Analysis and Sorting of Cells and Particles," *Rev. Sci. Instrum.*, 62(11):2751–2764 (1991).

Thomas et al., "Computer–Based Electronic Cell Volume Analysis with the AMAC II Transducer," *J. Histochem. Cytochem.*, 22(7):626–641 (1974).

\* cited by examiner

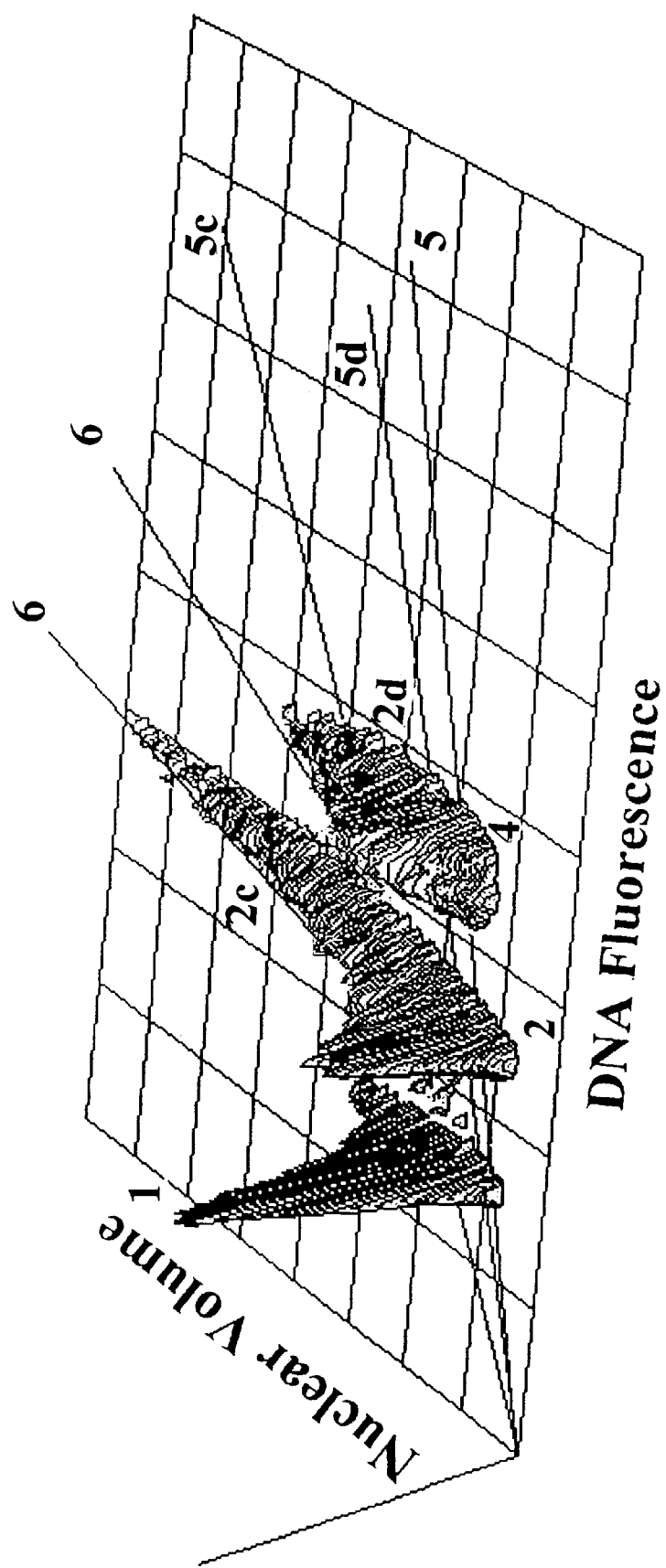

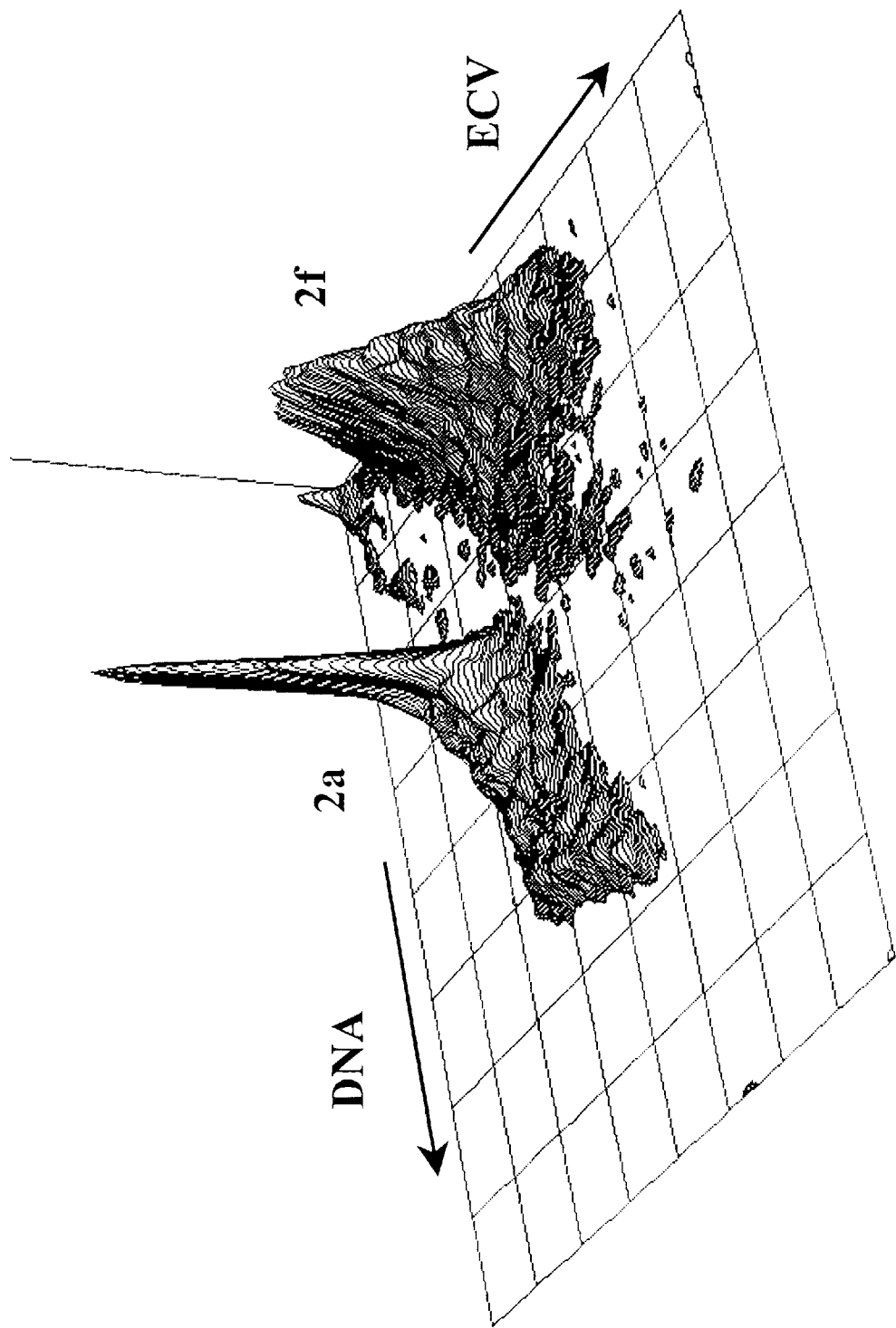

NUCLEAR PACKING EFFICIENCY

BACKGROUND OF THE INVENTION

1. Field of the Invention

The present invention relates to cell biology, and more particularly to characterizing a cell by its nuclear packing efficiency (NPE).

2. Background Information

Virtually all eucaryotic cells have a nucleus, a compartment enclosed by the nuclear membrane and containing most of the cell's DNA, as well as other nuclear components. Aberrations in the size and shape of the nucleus have long been recognized as an indication of cancer and other diseases, although their characterization was previously limited to microscopic observation.

Since then, attempts have been made to characterize cells by quantitating and comparing various nuclear components. For example, measurements of DNA, RNA and nuclear protein have been compared with each other. One study measured the quantity of DNA and tried to correlate it with measurements of the size of the nucleus, as measured by light scatter, time of flight and area. However, these correlations have been hampered by unreliable indirect estimates of the nuclear volume.

Indirect estimates of volume from diameter measurements using light scatter have worked best assuming uniform spherical particles of a certain size range and having a relatively high index of refraction. But this technique becomes less accurate when applied to nonideal biological samples outside the optimal range of measurement. Other measurements, termed "time-of-flight" or TOF, measure the size of particles as a flowstream carries the particles across a beam of light. However, this technique is subject to many limitations, including sensitivity to fluctuations in the speed of the particles and variations from the relative orientation of the particles, and only yields a measurement of one axis of the three-dimensional particle.

Still other indirect measurements estimate nuclear volume based on the cross-sectional areas of the nucleus. But these measurements, in turn, can be limited by variability in the staining and mounting techniques used on the nuclei. In particular, confocal microscopes have been used to measure the area of stained DNA in the nucleus, summing up successive cross-sections to obtain a measure of the total DNA. By assuming that the nuclear volume is proportional to the stained DNA, this technique then yields an estimate of the nuclear volume. However, this technique fails to account for the granularity of DNA within in the nucleus, and ignores the varying contribution to nuclear volume from the other components of the nucleus: RNA, nuclear proteins, nuclear lipids, nuclear envelope and nuclear water.

Thus, previous techniques fail to meet the need for satisfactory measurements of nuclear volume in combination with a useful correlation with other measurements to characterize the condition of nuclei and the cells as a whole. The present invention satisfies this need and provides related advantages as well.

SUMMARY OF THE INVENTION

The nucleus of a cell is a highly organized structure, allowing precursor materials to pass through pores in the nuclear envelope into the nucleus, and nuclear products to be transported out to the cytoplasm. The complex nuclear machinery—nucleic acids, proteins, lipids and other components—are tightly packaged within the volume of the nucleus.

As with most organized structures in nature, the nucleus assumes a shape for compact packaging of its components for optimal efficiency. When a cell becomes diseased, such as in malignant cells, the nuclear organization breaks down. For example, the DNA loses its ability to fold efficiently around histone proteins into organized structures called nucleosomes. The protein content also changes, as well as other biochemical components of the nucleus. The volume of the nucleus becomes forced to increase to accommodate this disorganization. Thus, the efficiency of this packing is a characteristic of the nucleus—and a useful indication of the condition of the cell as a whole.

The present invention provides methods and devices for determining the nuclear packing efficiency (NPE) of a cell by measuring the spatial displacement of the nucleus (SDN), for example by using flow cytometry to measure electronic nuclear volume (ENV). When the method is applied to procaryotes or viruses, the SDN can be considered the volume of the surrounding particle, which is the procaryotic cell or the virus itself. One or more biochemical components (BCs) of the nucleus are also measured, such as nucleic acids, nuclear protein, nuclear lipids or nuclear water. An NPE is then determined by correlating the values measured for BC and SDN.

A variety of techniques can be used to correlate the BC and SDN to yield an NPE. Polynomial fitting can be used, from the ratio BC/SDN to more complex expressions such as $NPE = k_1(BC)^a/(SDN)^b + k_2(BC)^c + k_3(SDN)^d + k_4$. Graphical methods are particularly useful for evaluating NPEs for a population of cells and for identifying distinct subpopulations of cells. Subpopulations can then be characterized in terms of their geometric parameters, such as diameter, eccentricity and gradient line slope.

Once determined, NPEs are useful for identifying cells having a phenotype of interest. For example, cells can be identified by tissue source and by the sex and species of the organism, as well as by various states of differentiation and stages in the cell division cycle and apoptosis. NPEs can also identify cells having various disease states as they differ from their normal states, particularly neoplastic cells exhibiting aneuploidy, distinguishing among benign, malignant and metastatic cells, thus enabling the diagnosis and prognosis of cancer.

BRIEF DESCRIPTION OF THE DRAWINGS

FIGS. 1a to 1c show NPE contours (electronic nuclear volume v. DNA fluorescence) for normal human cells from surface oral epithelium (FIG. 1a), intestine (FIG. 1b) and thyroid (FIG. 1c). NPE contours for other normal human cells are shown in FIGS. 2a, 3a and 5a.

FIGS. 4a to 4f show NPE contours for human cells taken from four cancerous tissue sources: gastric (FIG. 4a and perspective view FIG. 4b), prostate (FIG. 4c), ovarian (FIG. 4d and perspective view FIG. 4e) and lung (FIG. 4f).

Figure 1A:
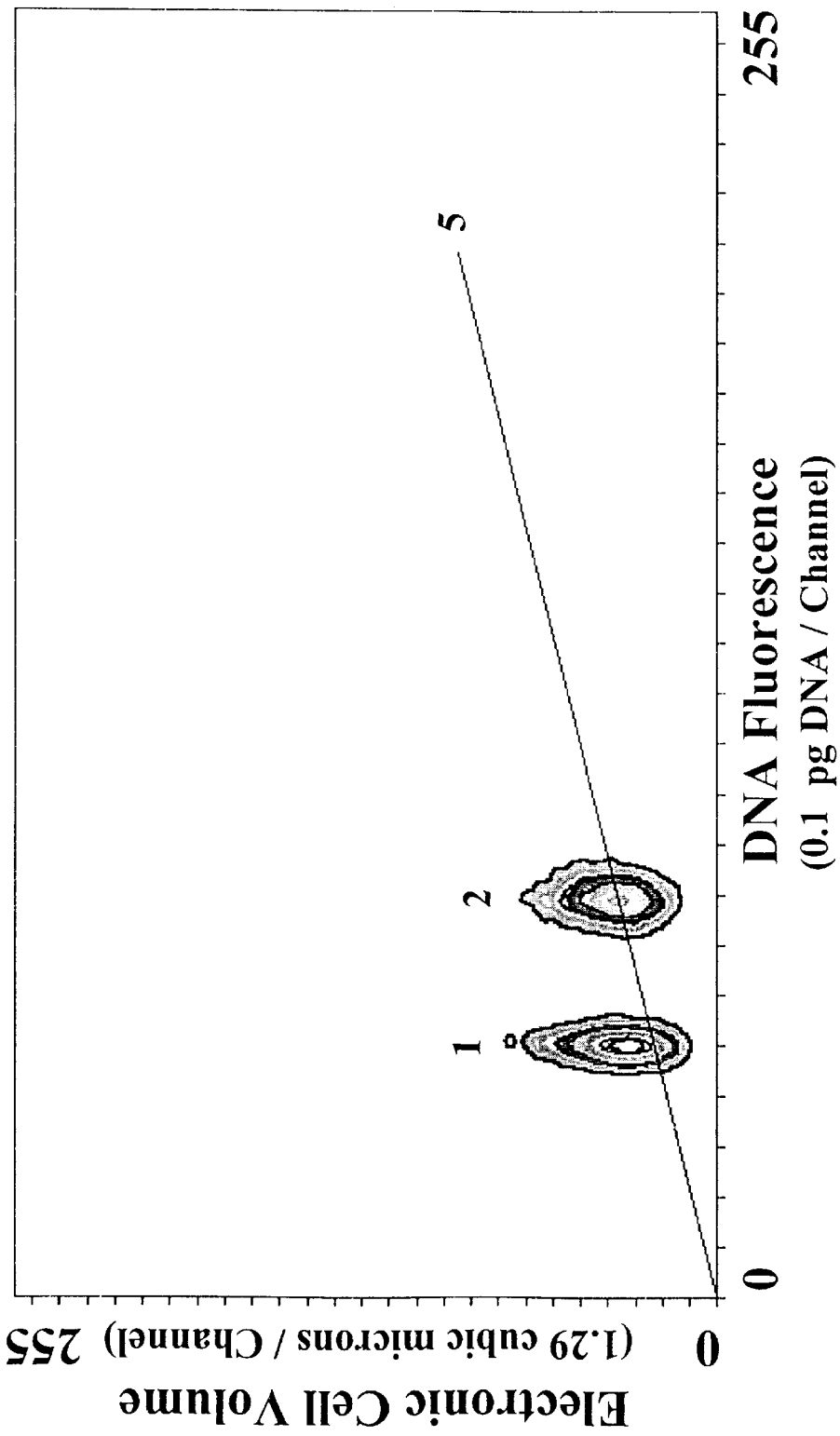
Figure 1B:
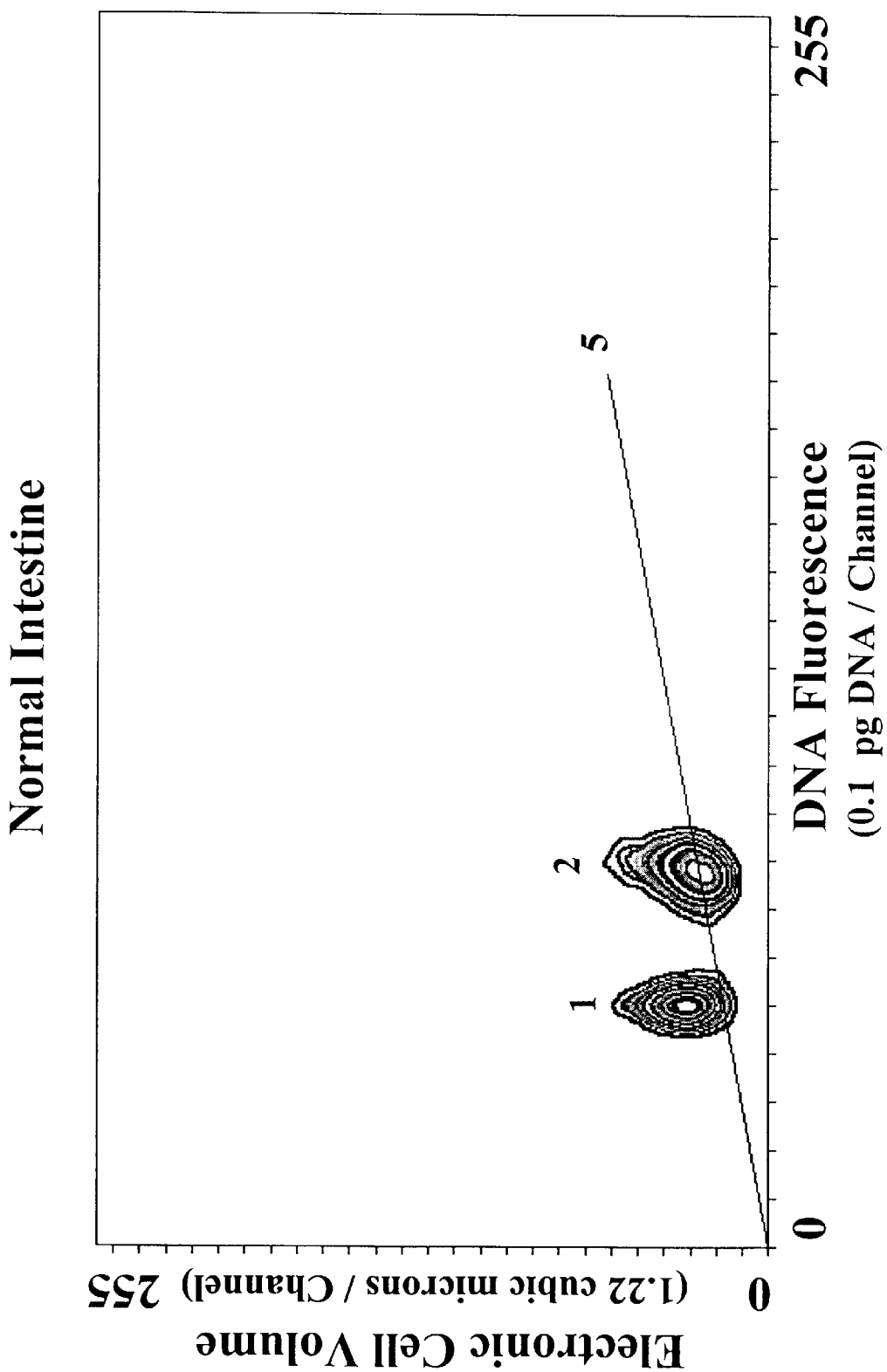
Figure 1C:
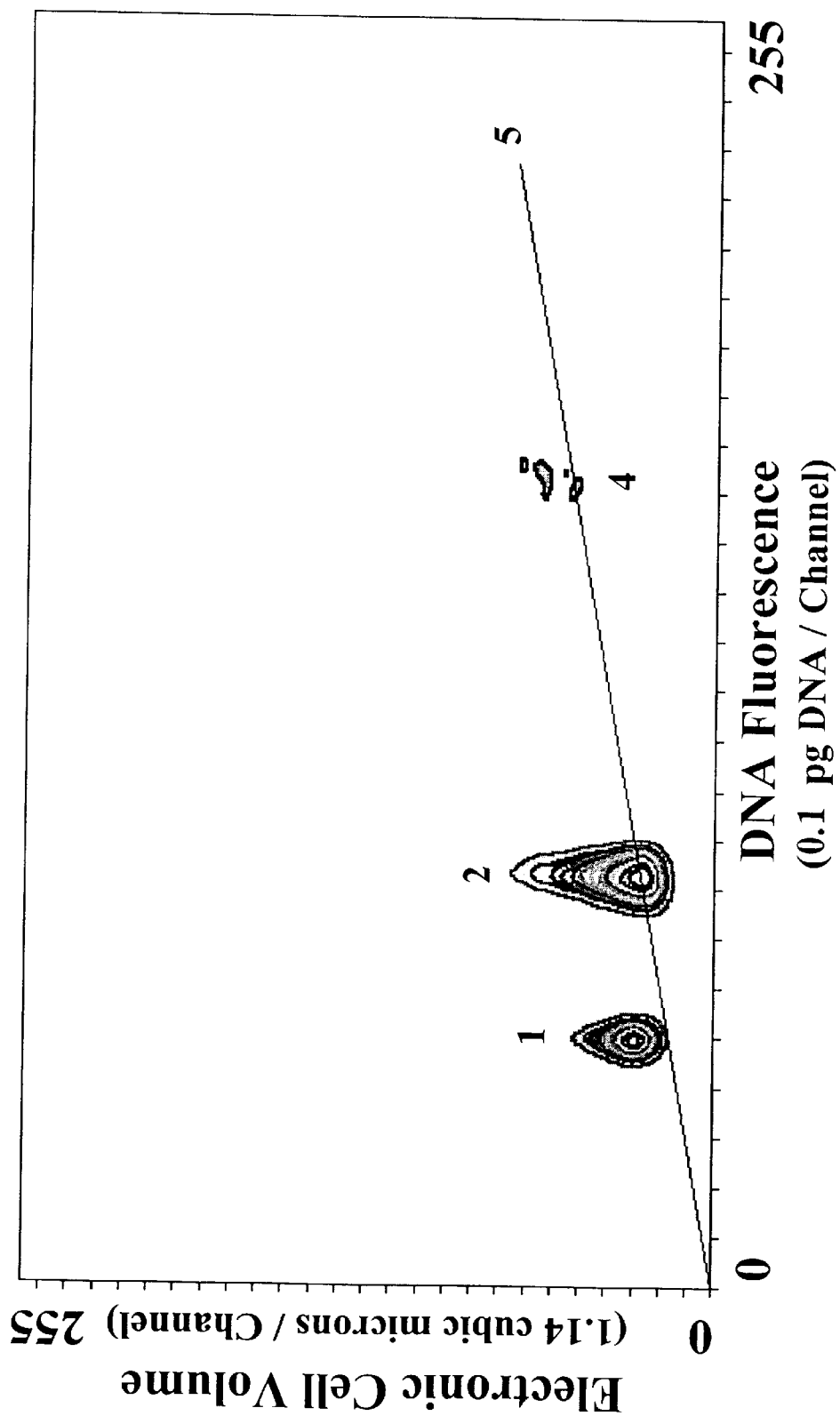

In the figures, the following reference numbers are used:

1 trout red blood cell nuclei (TRBC) internal standard
2 diploid $G_0/G_1$ cluster
   2a cluster of diploid $G_0$ cells
   2b cluster of diploid $G_1$ cells
   2c cluster of aneuploid $G_0$ cells
   2d second cluster of aneuploid $G_0$ cells
   2e cluster of activated lymphocytes
   2f cluster of apoptotic cells
3 diploid cells in S phase
   3c cluster of aneuploid S cells
4 diploid $G_2$+M cluster
   4a cluster of diploid $G_2$ cells
   4b cluster of diploid M cells
   4c cluster of aneuploid $G_2$+M cells
5 normal diploid NPE line
   5c aneuploid NPE line
   5d second aneuploid NPE line
   5f apoptotic NPE line
6 gradient line for cluster
   6e gradient line for activated lymphocytes Not all clusters may be visible in a given contour due to the particular threshold values selected for display and printout.

DETAILED DESCRIPTION OF THE INVENTION

The components of the nucleus of a cell are packaged within the volume of the nucleus. The efficiency of this packing is a characteristic of the nucleus—and a useful indication of the condition of the cell as a whole. Thus, the present invention provides a method for determining the nuclear packing efficiency (NPE) of a cell. The method measures the spatial displacement of the nucleus (SDN) and one or more biochemical components (BCs) of the nucleus. The NPE is then determined by correlating the values of SDN and the BCs.

"Spatial displacement of a nucleus" (SDN) as used herein means the volume of space that is occupied by the nucleus. By occupying that volume, the nucleus can be said to displace any non-nuclear matter that would have otherwise occupied that space.

"Nucleus" as used herein generally means the organelle surrounded by the cytoplasm of the eucaryotic cell that contains the chromosomal DNA. The term encompasses the inner and outer walls of the nuclear envelope and their associated proteins.

In addition to eucaryotic cells, the NPE can also be applied to procaryotic cells, which lack a nucleus in the eucaryotic sense. In this context the term "nucleus" is therefore used to refer to the particle size of the entire procaryotic cell itself. Thus, references to "nuclear" volume or spatial displacement can refer to the volume or spatial displacement of the procaryotic cell. Similarly, biochemical components of the "nucleus" can also refer to cellular components of procaryotic cells.

Furthermore, the NPE can be applied to viruses. Because viruses are not considered cells, the term "nucleus" in this context can refer to the particle size of the entire virus or of a portion such as a capsid. Thus, references to spatial displacement volume of a "nucleus" and biochemical components of the "nucleus" in the context of viruses should be understood to refer to the volume and components of the vital particle as a whole. Volume determination for viruses is well known in the art (DeBlois and Wesley, *J. Virol.* 23:227–233 (1977).

The electronic cell volume (ECV) method is a particularly useful method for measuring SDN, yielding an "electronic nuclear volume" (ENV). As used herein, the term "ENV" means the volume of the nucleus as determined by an ECV method. When determining ECV, particles such as nuclei are suspended in a conducting fluid, which is passed through a small aperture. An electric field, either DC or AC, is then applied across the aperture, causing current to flow through the aperture. When a particle passes through the aperture, the current is disrupted, causing a measurable pulse in the current. This pulse can be used to count individual particles as they pass through the aperture. The dimensions of the pulse can also be related to the size of the particle.

Refinements of the basic ECV method include shaping the inlet and outlet volumes of the measuring aperture to reduce edge effects and to produce a linear relationship between the measured change in current and the volume of the particle. A particularly useful method for measuring ENV is described in U.S. Pat. No. 4,818,103, to Thomas, which describes an improved flow cytometry aperture.

Compared to previous methods, such as forward angle light scatter, the ECV method is not significantly affected by the shape of the particles as they are carried in the fluid. This is particularly important when the particles can be nonspherical, such as biological particles injected into the center of the stream. A useful method uses a time-of-flight (TOF) signal to account for such changes, as described in U.S. Pat. No. 4,298,836 to Groves. The TOF measurements can be taken from the optical fluorescent pulse generated by the nucleus as it traverses an excitation light beam, or directly from the ECV pulse. The width of the pulse is related to the long axis of the particle.

An SDN can be expressed in terms of volume such as cubic microns or cubic millimeters. An SDN can also be expressed in terms of a signal generated from an ECV device, whether analog or digital. In the Figures and Examples below, the ENV may be expressed as an 8-bit value, providing 256 channels of resolution. Nevertheless, the conversion from channels to cubic microns is provided in each figure. However expressed, the SDN is then correlated with BC measurements to determine the NPE. It should also be noted that the method does not require that the SDN and the BCs be measured in any particular order.

"Biochemical component" (BC) as used herein means any identifiable substance in the cell that can be quantitated in physical terms. For example, a BC can be measured in terms of amount, volume or area, such as surface or cross-sectional area. Examples of BCs include various nucleic acids such as DNA and RNA, proteins, lipids and nuclear water, as well as mixtures and subsets of individual BCs.

DNA in a nucleus can be conveniently measured by flow cytometry methods. Flow cytometry methods are generally described in M. G. Ormerod, *Flow Cytometry* (BIOS Sci. Pubs., 2nd ed. 1999, and referenced cited therein). When nuclei are treated with a DNA stain, such as a fluorescent stain, the quantity of DNA in the nuclei can be measured by detecting the amount of staining or fluorescence. DNA stains include propidium iodide, acridine orange, ethidium bromide, quinacrine, mithramycin, chromomycin A3 and 4',6-diamidino-2-phenylindole (DAPI) (see Krishan, *J. Cell Biol.* 66:188–193 (1975); Darzynkiewicz et al., *Cytometry* 5:355–363 (1984); Kapuscinski, *Biotechnic & Histochem.* 70(5):220–233 (1995)) (see Example I). Automated microscopes that measure absorption or fluorescence can also be used with DNA staining to measure the quantity of DNA in the cell nucleus (Tanke et al., *J. Histochem. Cytochem.* 27:84–86 (1979); Bjelkenkrantz, *Histochemistry* 79(2):177–91 (1983)).

Indirect measurements of DNA are possible by measuring the proteins and other components associated with DNA structures in the nucleus. Chromosomal DNA is coiled around octomers of histone proteins (two each of H2A, H2B, H3 and H4) to form a complex termed a nucleosome. Together with nonhistone chromosomal proteins, DNA-histone structures form fibers collectively termed chromatin, which is itself divided into metabolically active euchromatin and transcriptionally inert heterochromatin. Measurement of any of these DNA-associated proteins can therefore be a useful measure of DNA content. For example, labeled antibodies that specifically bind to any of these proteins are particularly useful for such indirect measurements of nuclear DNA. In particular, histones be measured by flow cytometry and automated microscopes using antibodies against specific histones (Miller et al., *Hybridoma* 12(6):689–698 (1993)). Histones can also be quantitated by electrophoretic examination using a silver stain (Tsutsui et al., *Anal. Biochem.* 146(1):111–117 (1985)).

RNA has similarly been measured with flow cytometry using acridine orange staining (Piwnicka et al., *Cytometry* 3(4):269–75 (1983)). RNA can also be measured by cytophotometric image analysis using methyl green-pyronin Y stain (Schulte et al., *Histomchem. J.* 24(6):305–310 (1992)). As with DNA, RNA-related proteins, such as nuclear proteins related to RNA transcription, can be used to measure RNA indirectly.

The nucleolus is another nucleic-acid-related BC, a large structure where large numbers of rRNA copies are transcribed and immediately packaged with ribosomal proteins to form ribosomes. Thus, antibodies against any of the nucleolus machinery can provide a useful BC for measurement.

Lipids that are BCs include any measurable lipids in the nucleus such as nuclear envelope lipid, whether in the inside or outside walls. These lipids can be measured directly or indirectly by measuring nuclear-envelope-associated proteins. Outer wall nuclear membrane proteins include ribosomes. Proteins associated with the inner wall of the nuclear membrane include nuclear pore proteins, nuclear lamina proteins and lamina-associated polypeptides. Fluorescent lipophilic dyes (Collas et al., *Dev. Biol.* 169(1):123–35 (1995)) and monoclonal antibodies that recognize the nuclear pore antigens (Matsouoka et al., *Biochem. Biophys. Res. Commun.* 254(2):417–423 (1999)) can be used to measure various components of the nuclear envelope and to provide a measure of lipid content, as well.

Although proteins have been discussed as a means to indirectly measure nucleic acids and lipids, nuclear proteins can be BCs in their own right. Nuclear proteins can be detected by nonspecific staining using FITC fluorescence in combination with flow cytometry (Roti et al., *Cytometry* 3(2):91–96 (1982)). Another method is to measure dinitrofluorobenzene (DNF) absorbance using cytophotometric image analysis (Cohn et al., *Histochemistry* 79(3):353–364 (1983). Yet another method is to measure protein-bound sulfhydryl groups with the fluorescence of AEDANS (Schabronath et al., *Cytometry* 11(3):333–340 (1990)).

Nuclear Matrix Proteins (NMPs) and other specific nuclear proteins can also be measured as BCs. NMPs can be measured using antibodies prepared against purified protein molecules located in the nuclear matrix. As with the antibodies discussed above, they can then be conjugated with fluorescent stains and used with flow cytometry or immunohistochemical staining to detect specific NMPs (Hughes et al., *Am. J. Clin. Path.* 111(2):267–274 (1999)).

Nuclear water and associated non-organic salts make up the remainder of the volume in the nucleus. Nuclear water can be measured by ENV when performed at isotonic and iso-osmotic conditions.

As disclosed above, an NPE is determined by correlating the SDN and BC values. This correlation may be achieved by a variety of mathematical functions and operations. For example, the NPE can be determined by using a general polynomial function such as $$NPE = k_1(BC)^a/(SDN)^b + k_2(BC)^c + k_3(SDN)^d + k_4.$$

In this formula, $k_1$, $k_2$, $k_3$, $k_4$, a, b, c and d are individually preselected constants and $k_1$ is not zero. Particularly useful values for $k_1$, $k_2$, $k_3$, $k_4$, a, b, c and d are 2, 1, ½, 0, -½, -1, and -2 independently, with the proviso that $k_1$ is not zero. A specific application of the general formula is where each of $k_1$, a and b are 1 and each of $k_2$, $k_3$ and $k_4$ are zero, resulting in the ratio $$NPE = BC/SDN.$$

Determination of an NPE is not limited to measuring and correlating a single BC, however.

A second biochemical component ($BC_2$) can be measured as a further step in the method. The $BC_2$ can be any of the BCs disclosed above, such as nucleic acids, lipids, proteins and nuclear water, so long as it is different from the first BC. $BC_2$ can then be incorporated into the determination of NPE by a variety of formulas using the expression $k_5(BC_2)^e$, where $k_5$ and e are each preselected constants such as 2, 1, ½, 0, -½, -1 and -2. For example, $k_5(BC_2)^e$ can be added to the value of BC in the general formula, so that the general formula becomes $$NPE = k_1(BC + k_5(BC_2)^e)^a/(SDN)^b + k_2(BC + k_5(BC_2)^e)^c + k_3(SDN)^d + k_4.$$

Similarly, $k_5(BC_2)^e$ can be added to the value of SDN in the general formula to obtain $$NPE = k_1(BC)^a/(SDN + k_5(BC_2)^e)^b + k_2(BC)^c + k_3(SDN + k_5(BC_2)^e)^d + k_4.$$

Furthermore, the NPE obtained by the general polynomial formula can be multiplied by $k_5(BC_2)^e$:

$$NPE = k_5(BC_2)^e \times (k_1(BC)^a/(SDN)^b + k_2(BC)^c + k_3(SDN)^d + k_4).$$

The polynomial expressions above are merely intended to illustrate the range of useful correlations possible between BCs and SDN. Specific examples of NPE correlations include the following:

NPE=DNA/ENV

NPE=(fluorescence of DNA)/ENV

NPE=DNA/ENV$^{1/2}$

NPE=DNA/(procaryotic cell volume)

NPE=RNA/(volume of viral particle)

NPE=NMP/ENV
NPE=(mass of nucleosome)/ENV
NPE=(volume of nuclear envelope)/ENV
NPE=(DNA−RNA)/ENV
NPE=(DNA+RNA)/ENV$^2$
NPE=(DNA×RNA)/ENV$^2$
NPE=DNA/(ENV−(nuclear water))
NPE=(DNA+nuclear matrix protein)/ENV
NPE=DNA$^{-1}$/(ENV+RNA)$^{-1}$
NPE=(DNA+RNA)/ENV$^2$
NPE=2(DNA)$^2$/ENV+0.5(DNA)−ENV$^2$+5
NPE=(DNA+RNA)$^2$/ENV−(DNA+RNA)$^{1/2}$+ENV Mathematical variations of these correlations between BC and SDN can include trigonometric, logarithmic and exponential and other transcendental functions while not falling within the strict formula of the polynomial itself. These variations should be considered equivalent so long as they mathematically relate BC and SDN in a substantially similar way to achieve a substantially similar correlation that is a useful measure of NPE. Thus, determining NPE is not limited to functions, however, but can be determined using a number of more sophisticated methods.

Graphical methods provide a powerful tool for determining and visualizing NPEs (see Examples II.D and III). As an example, a BC and SDN can be measured for a cell and plotted on separate axes for BC and SDN, resulting in a datapoint for the cell. The term "datapoint" means herein any mathematical correlation between two or more values. Thus, a datapoint for a cell can also correlate DNA, RNA and SDN. The term can refer to a graphed or plotted point, but can also refer to any representation of the values of BC and SDN, whether displayed visually, represented numerically or stored in a computer's memory. However, each datapoint's values should represent a single cell or small group of cells.

Datapoints for multiple cells can also be plotted, either separately or on the same plot. If on the same plot, the datapoints can be represented by a variety of graphical methods. Scattergrams simply show each datapoint on the same graph, where the density of datapoints reflects the number of cells having BCs and SDNs of a certain value or range. Contour plots can be used illustrate the frequency of datapoints in a certain range by plotting a contour or surface, where a separate axis is used to indicate frequency.

Figure 2A:
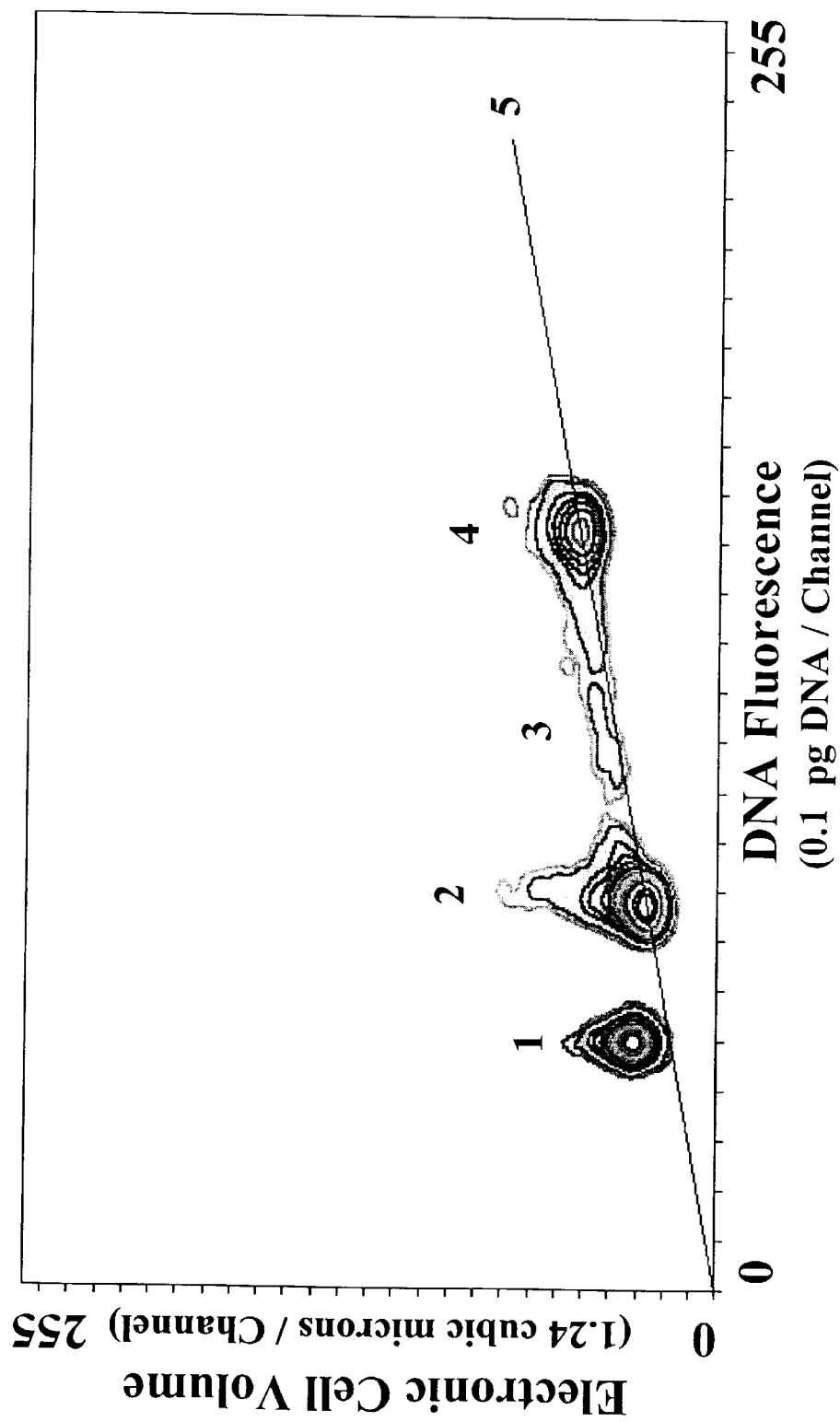
FIGS. 2a to 2e compare NPE contours for human lymph node and breast cells in various states: normal human lymph node cells (FIG. 2a and perspective view FIG. 2b), cells from a benign breast tumor (FIG. 2c), cells taken from a malignant primary tumor from breast tissue (FIG. 2d) and cells taken from metastasizing breast cells from the tumor shown in FIG. 2d to the lymph node (FIG. 2e).
Figure 2B:
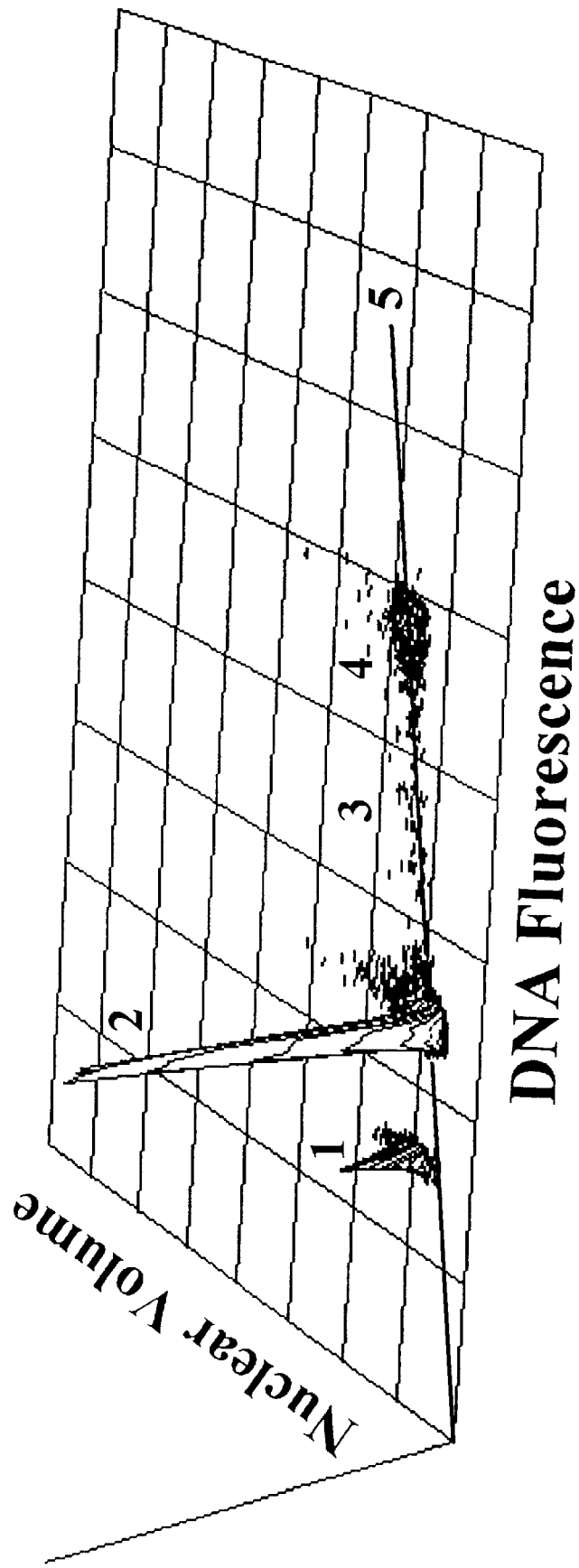

An example of a graphical representation of datapoints is FIG. 2b, which shows data from normal human lymph node. The horizontal axis is DNA fluorescence, reflecting the amount of DNA in each nucleus, and the depth axis is ENV, reflecting nuclear volume. The vertical axis is the number of cells having a datapoint at each given value on the horizontal and depth axes. Thus, a frequency contour is provided for ENV v. DNA.

As shown in this perspective view, the majority of the lymph node cells are in a single peak representing a cluster of cells 2 that are diploid $G_0/G_1$ cells. The second highest peak represents a cluster of trout red blood cell nuclei (TRBC) 1 added to the sample as an internal control (see Example I.C.). A much smaller peak is also visible representing a cluster of diploid $G_2$+M cells 4 in the sample of lymph node cells.

The same data can be represented in a contour graph. In FIG. 2a, the horizontal axis is DNA fluorescence and the vertical axis is ENV. The frequency of cells having each ENV v. DNA data point is shown by contour lines, representing lines of equal frequency, much as a topographic map uses lines of equal elevation. As before, the cluster of TRBC internal standard 1 is seen, as well as clusters representing the two subpopulations of lymph node cells: diploid $G_0/G_1$ cells 2 and diploid $G_2$+M cells 4.

Surprisingly, a line 5 can be drawn from the origin through the centers of the clusters 2 and 4. This is because the two clusters share a common correlation between ENV and DNA, even though the individual values for ENV and DNA differ by about two-fold. In short, the two clusters of lymph node cells share a common NPE that is characteristic for lymph node cells. In graphical terms, where a line has the formula BC=NPE(SDN), the slope of the line (NPE) is BC/SDN. Alternatively, the line can have the formula SDN=NPE(BC), where the slope (NPE) is SDN/BC. A line or substantially linear curve representing NPE can be determined graphically by hand, by calculator or determined by a variety of mathematical and statistical software packages. Thus, an NPE can be determined graphically for datapoints representing multiple cells.

An added advantage to representing the datapoints graphically is that distinct clusters of datapoints can be identified, each representing subpopulations of cells in the original sample. For example in FIG. 2a, clusters 2 and 4 are readily identified with separate subpopulations of cells. The term "cluster" means herein any subset of the entire set of datapoints plotted for a population of cells or for a representative number of cells in a preselected population. Similarly, the term "subpopulation" means herein the cells represented by the datapoints in a cluster. Thus, in FIG. 6a, separate subpopulations of cells can be discerned by clusters 2a, 2b, 3, 4a and 4b. It should be noted, however, that when virtually all the datapoints form a well-defined group, cluster 2 in FIG. 1a for example, the terms cluster and subpopulation may still apply.

More formally, a cluster can be defined as a neighborhood of datapoints that are adjacent to a local maximum of datapoints and characterized by decreasing frequency as the distance from the local maximum increases. If desired, a frequency threshold or cut-off can be used to further resolve the separation between clusters, and the subpopulations represented by the clusters.

Geometric parameters can then used to describe the characteristics of each cluster. The term "geometric parameter" means herein any geometric or mathematical property of a cluster. The center of a roughly circular cluster is a parameter that can be defined as the average center point, the centroid or the local maximum. The slope of a line passing through the origin and the center of a cluster is a particularly useful parameter. Where the shape of the subpopulation contour is ellipsoid, other useful geometric parameters include the eccentricity, the maximum range of the major axis, the maximum range of the minor axis and the standard deviations of the major and minor axes. Another useful geometric parameter is the perimeter of the cluster when represented graphically at a predetermined threshold value.

Other mathematical variations of these geometrical parameters for clusters can include a variety of polynomial, trigonometric, logarithmic, exponential and other transcendental functions, while not falling within the list of parameters described above These variations should be considered equivalent so long as they mathematically describe a geometrical feature of the cluster in a substantially similar way to achieve a substantially similar description that is a useful description of the cluster.

A gradient line is another particularly useful geometric parameter, indicating the general tilt of an ellipsoid or elongated cluster. The term "gradient line" means the line passing orthogonally through the direction of highest slope in a cluster. Examples of gradient lines are the lines marked 6 in FIG. 2d. The line orthogonal to the gradient line can also be a useful geometric parameter of a cluster. Although a gradient line can often be hand-drawn by inspection, the line can be determined more precisely by performing a linear regression of the datapoints in the subpopulation.

Having generated a contour of datapoints and identified clusters representing subpopulations of cells in the sample, the geometric parameters identified can then be used to identify different cells within a population of cells by identifying the cell if the cell's NPE is within at least one predetermined NPE range. Separately or concurrently, the method can further involve segregating the identified cell from non-identified cells. The term "segregating" herein means to separate the cells into distinctly separate areas or containers and are not in their original state or in a uniform mixture.

It should be emphasized that the methods for determining an NPE for a population of cells are not limited to graphical, but can be performed equally well numerically. Thus, each of the steps of the disclosed method for determining an NPE for a population of cells—including determining a datapoint for BC and SDN, identifying a cluster of datapoints and determining an NPE according to a preselected geometric parameter—can be performed numerically. For example, these steps can be performed by a computer without necessarily representing the data in graphical form. Thus, disclosed applications for NPEs and NPE contours should be understood to apply equally to both.

NPEs and NPE contours can be used to identify having a phenotype of interest. Cells can be identified by comparing their NPEs with other NPEs. For example, an NPE of a cell of interest can be compared with a predefined range of NPEs for a reference population of cells, or against other cells in the sample. As a result, NPEs and NPE contours are a useful characteristic to identify the phenotype of cells in a sample.

A particular use for NPEs is to determine the sex of an organism by its cells. In the somatic cells of many species, cells from female animals have two X chromosomes, while cells from male animals have one X and a smaller Y chromosome. As a result, male cells have less DNA content than female cells, but with comparable nuclear volumes. This difference is reflected by a lower packing efficiency. In FIG. 2a, cluster 2 tends to have a lower DNA content (DNA fluorescence channel closer to 76) when cells are from males and a higher DNA content (DNA fluorescence channel closer to 80.5) when the cells are from females. These changes are reflected in a higher slope (decreased NPE) for males and lower slope (increased NPE) for females. Thus, cells from animals of different sexes can be distinguished. The method is equally applicable in other animals, such as certain waterfowl, where the sex chromosomes are reversed.

NPEs can also be used to determine whether cells are from different tissues. For example, FIGS. 1a, 1b, 1c, 2a, 3a and 5a show NPE contours for cells from different tissues, each having characteristic NPEs. Thus, cells of unknown origin can also be identified by comparing their NPEs with NPEs of known tissues. Similarly, cells in different stages of differentiation can be identified by their NPEs (see Example III.C.).

A further use for NPEs is to determine whether cells are from different species. In FIG. 1a, for example, the NPE for nuclei from trout are distinguished from an NPE for human lymph cells. Similarly, the NPEs of the clusters in FIG. 6, representing cells from a mouse cell line, are distinguishable from the NPE in FIG. 1a. Thus, cells from different species can be distinguished by their NPEs.

Cells in different stages of the cell division cycle can also be identified using NPE methods. Normally dividing cells undergo a well-defined series of stages to coordinate cell division into two daughter cells and the corresponding replication of DNA necessary to maintain a complete set of chromosomes for the daughter cells. During S ("synthesis") phase, a cell replicates its nuclear DNA, doubling the DNA content of the nucleus. After resting during $G_2$ phase, the nucleus divides during M ("mitosis") phase, evenly separating the replicated DNA, followed by cytokinesis, where the cell itself divides into separate daughter cells. Cell division is then followed by the $G_0$ and $G_1$ phases before initiating S phase again. As shown in Example III.D, NPEs can be used to identify cells in different stages of the cell cycle.

Because the NPE of a cell is maintained during the cell cycle so rigorously, it follows that disruptions of the condition and normal growth of a cell will be reflected in its NPE. Thus, the NPE can be used to identify cells in an apoptotic state, when the cells undergo apoptosis, programmed cell death (see Example III.E).

Furthermore, NPEs can be used to identify an abnormal conditions such as a pathology or disease state. Disease states include genetic diseases such as sickle cell anemia. For example, the extra chromosomes present from Down's syndrome and Klinefelter's syndrome can be detected using NPEs. Similarly, genetic anomalies. associated with autoimmune diseases can also be detected.

NPEs are particularly useful for identifying a neoplastic state. As used herein, the term "neoplastic" means characterized by formation and growth of abnormal tissue that grows more rapidly than normal. Neoplastic tissue can show partial or complete lack of structural organization and functional coordination with normal tissue. Neoplastic cells are often characterized by aneuploidy. The term "aneuploidy" herein means having an abnormal number of chromosomes. Aneuploid cells are contrasted with cells having a normal number of chromosomes, although the precise number can vary depending on the stage of division in the cell division cycle. Thus, the method can be useful for distinguishing neoplastic cells from normal tissue.

Figure 2C:
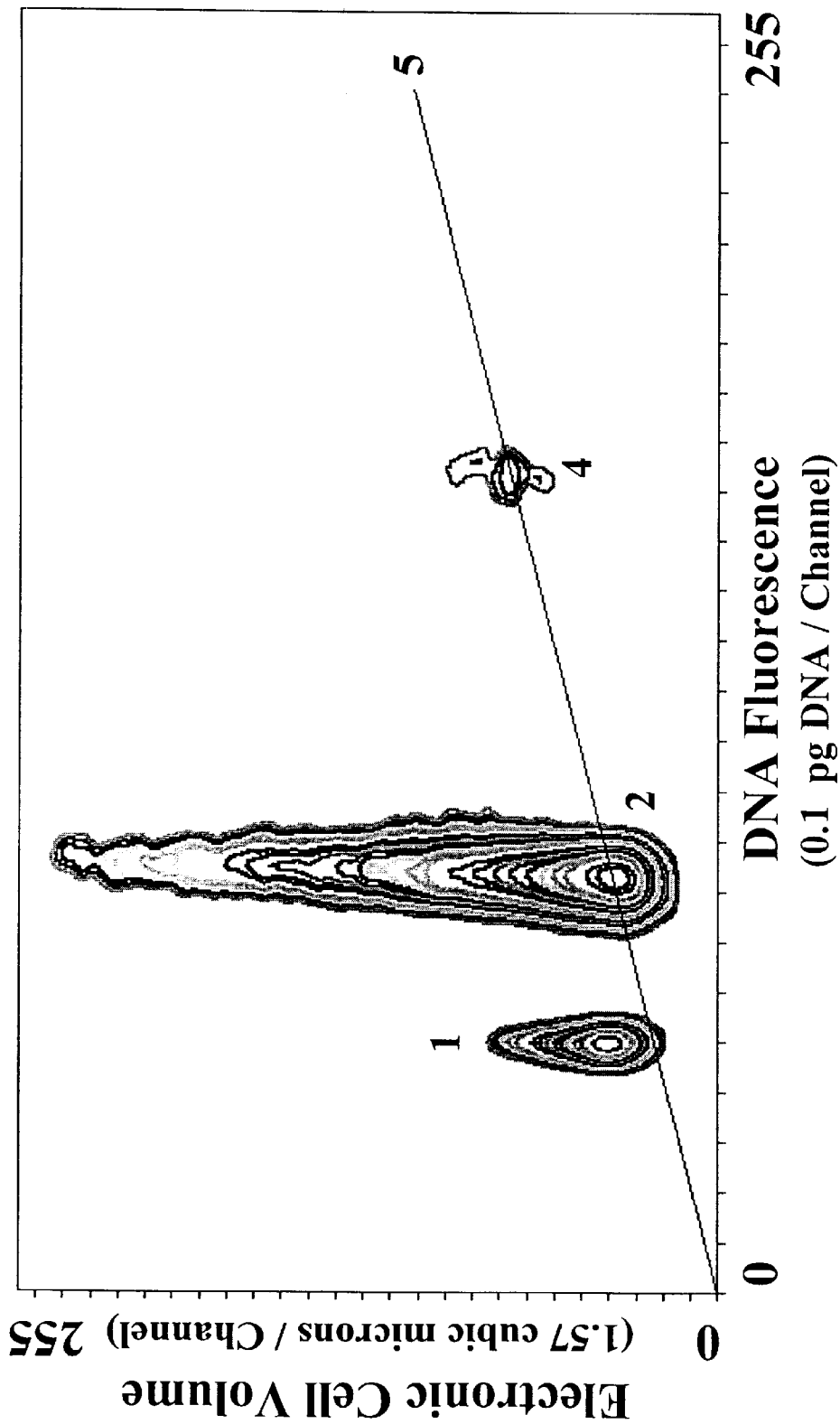
Figure 2D:
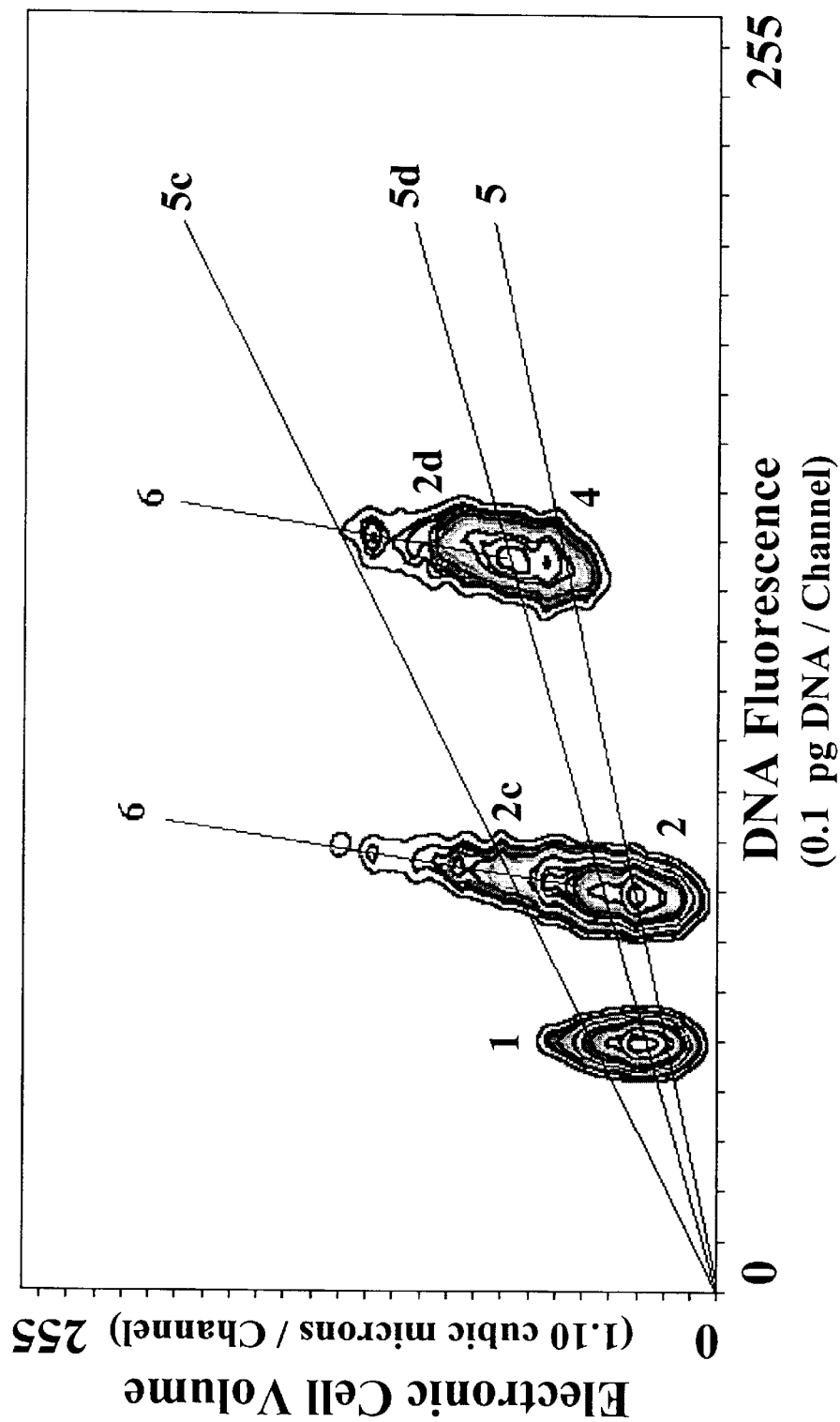
Figure 2E:
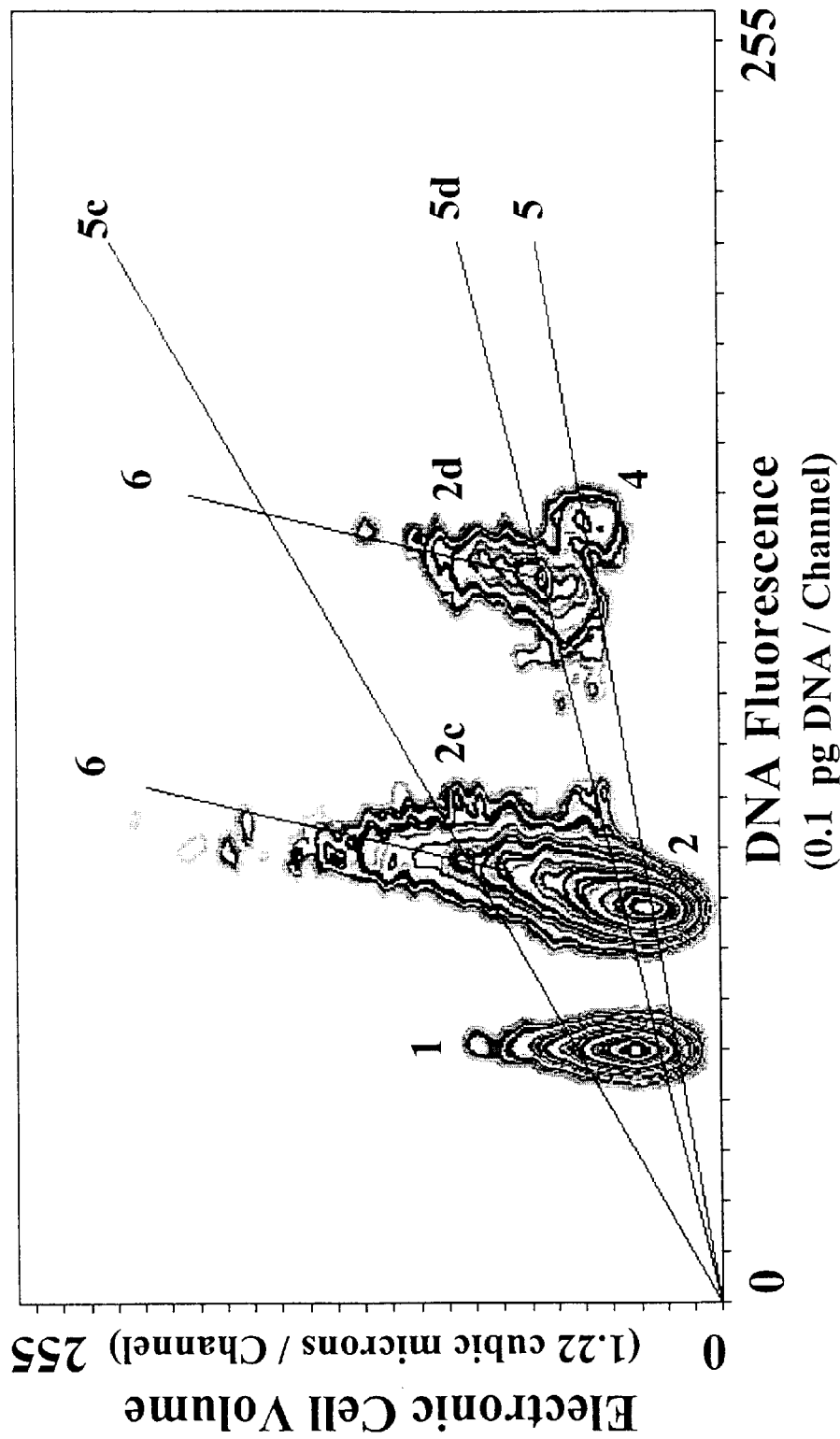

As discussed in Example III, normal cells (see FIG. 2a) can be characterized by relatively circular clusters, while neoplastic cells can be characterized by relatively elongated clusters (see FIGS. 2c, 2d, and 2e). The clusters can become elongated due to the presence of aneuploid cells, labeled 2c, 2d and 4c. In turn, these clusters of aneuploid cells can give rise to one or more aneuploid NPE lines 5c, 5d (see FIGS. 2d, 2e).

Among neoplastic cells, benign tumors can have clusters with relatively vertical gradient lines 6 (see FIG. 2c), while cells from malignant primary tumors (see FIGS. 2d and 3b) can have clusters with tilted gradient lines 6. In addition, if metastasis has occurred, the primary tumor clone can be identified by its tilted gradient line and its NPE in the metastatic site (see FIGS. 2d, 2e, 3b, 3c).

Figure 4A:
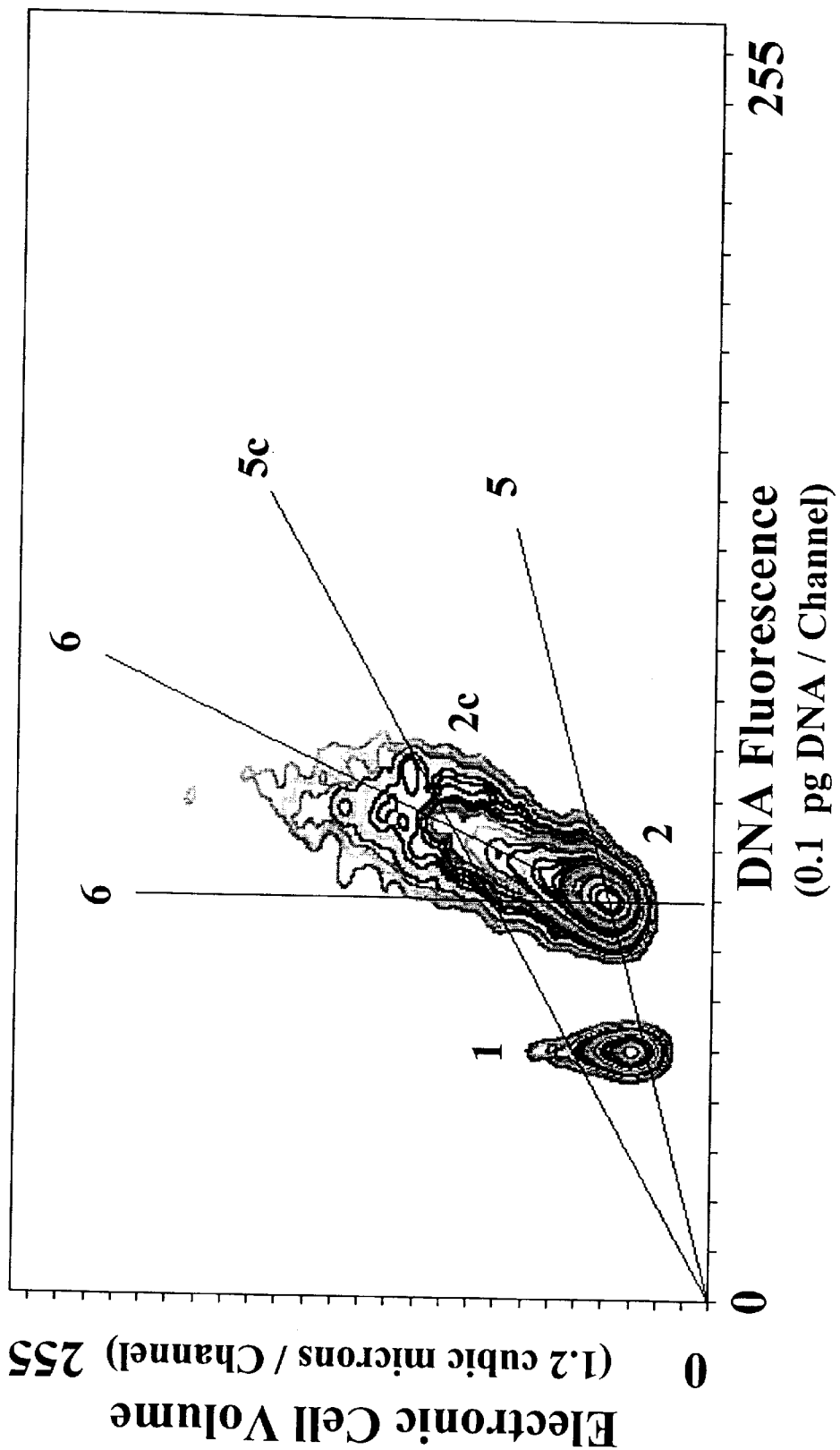
Figure 4B:
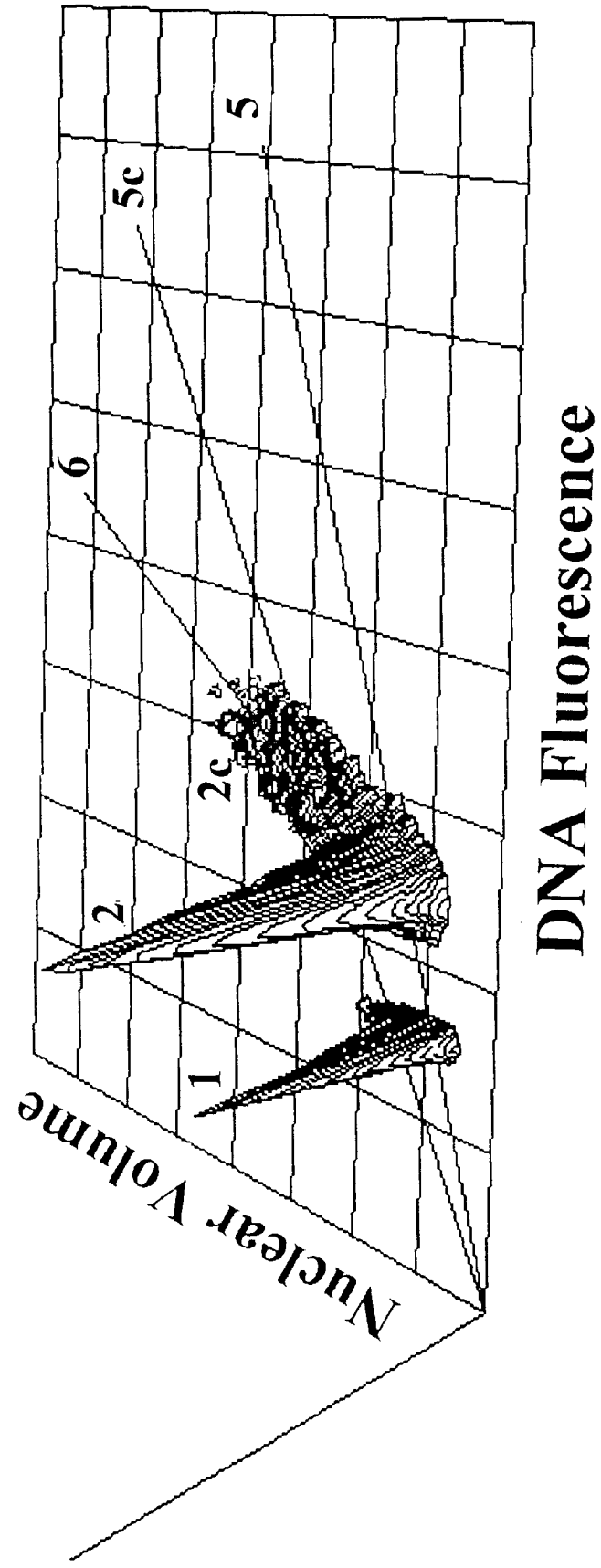

Furthermore, neoplastic cells can be characterized by having abnormal ratios of cells in the $G_0/G_1$ cluster 2 and $G_2$+M cluster 4. For example, $G_0/G_1$ cells 2 clearly predominate over the $G_2$+M cells 4 in the normal human lymph node cells shown in FIG. 2b. In the ovarian cancer cells in FIG. 4e, however, there are nearly equal numbers of $G_0/G_1$ diploid cells 2 and $G_2$+M diploid cells 4, indicating that the ratio of cells in the $G_2$ and M stage of the cell division cycle has become abnormal. Thus NPEs can be useful for identifying a neoplastic state in a perspective view.

These methods are applicable to any type of tissue subject to cancer, including lymph node (FIG. 2e), breast (FIGS. 2c, 2d), colon (FIGS. 3b and 3c), gastric (FIG. 4a), prostate (FIG. 4c), ovarian (FIG. 4d), lung (FIG. 4f), leukemia (FIG. 5b), as well as cervical and testicular tissue, pancreas, liver, brain and small intestine. Other tissues subject to these methods include brain, ovary, testes, bone and exfoliated circulatory tissue.

Figure 7:
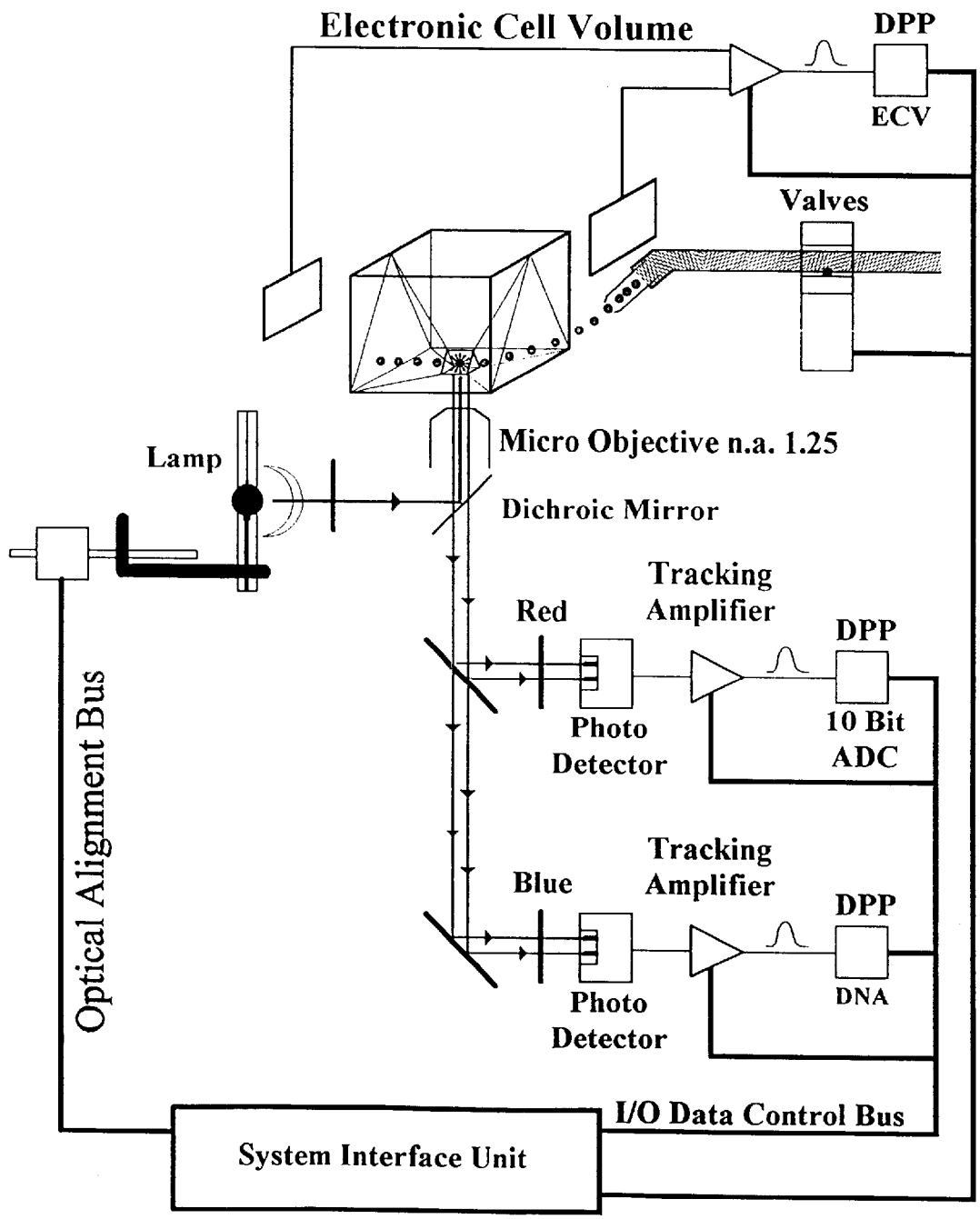
FIG. 7 shows a block diagram for a device for preforming the method of the invention.

Devices for performing the methods disclosed above are also provided by the present invention. A device for determining the NPE of a cell can have means for measuring one or more BCs and measuring SDN, and means for determining the NPE. A block diagram of such an embodiment of the device is shown in FIG. 7. Specific measuring means are discussed in detail above, in the examples below, and in the publications and patents cited herein.

Each of the publications and patents cited herein are hereby incorporated by reference. The term "comprising" as used herein, including its use in the body of the claims, is intended to be open-ended, thereby encompassing the recited elements or steps, as well as encompassing embodiments having additional elements or steps. The following examples are intended to illustrate but not limit the invention.

EXAMPLE I

Preparation of Stained Nuclei

The following examples illustrate the preparation of isolated nuclei from tissue samples.

A. From Solid Tissue

Isolated nuclei from solid tissue specimens were prepared as follows. Approximately 1 to 2 cubic millimeters of tissue was placed in a petri dish with 2 ml of the following nuclear isolation solution to isolate and stain the nuclei: 10 mg/ml 4',6-diamidino-2-phenylindole (DAPI) DNA stain (Sigma Chemical Co.; St. Louis, Mo.); 0.6% NP-40 (v/v) (Accurate Scientific & Chemical Co.; Hicksville N.Y.); in isotonic phosphate buffered saline solution at pH 7.2. The isolated stained nuclei were filtered through a 35 micron polypropylene filter (RATCOM, Inc.; Miami Fla.) and placed on ice. Using this method, samples of isolated, stained nuclei were prepared from a variety of solid tissue sources, including lymph node, intestine, breast, colon, thyroid, ovary, prostate, stomach and surface epithelial cells from mouth.

B. Human Lymphocytes

Human lymphocytes were isolated from venous whole blood using ficoll hypate, washed with isotonic saline, and adjusted to a concentration of about $1 \times 10^7$ lymphocytes/ml. Then, 0.1 ml of this lymphocyte solution was added to 1 ml of the nuclear isolation solution described above, resulting in a solution of lymphocyte nuclei at a concentration of approximately $1 \times 10^6$ nuclei/ml. The stained nuclei were filtered through a 35 micron polypropylene filter and placed on ice.

C. Trout Red Blood Cell Nuclei (TRBC)

Nuclei from trout red blood cells were used as an internal standard. Trout (*Salmo gairdnerii irideus*) red blood cells (U.S. Fish Hatchery; Erwin Tenn.) were prepared into stock solutions as follows: 150 μl of a commercially available TRBC solution (RATCOM Inc.; Miami Fla.) was added to 2 ml nuclear isolation solution described above, resulting in a stock solution of TRBC nuclei at a concentration of about $2 \times 10^6$ nuclei/ml. The stained TRBC nuclei were then filtered through a 35 micron polypropylene filter and placed on ice.

EXAMPLE II

Determination of NPEs

A. DNAnalyzer Flow Cytbmeter

The DNAnalyzer™ flow cytometer (RATCOM Inc.; Miami Fla.) simultaneously analyzed the DNA content by fluorescence and the volume of each particle (ENV) as it passed through the measuring aperture of the instrument. The volume was determined by the Coulter Electronic Cell Volume principle described in U.S. Pat. No. 2,656,508 to Coulter, and according to the teaching in U.S. Pat. No. 4,818,103 to Thomas and Eggleston.

The DNAnalyzer used a unique equilateral triangle flow cell with a cross-section of 70 microns per side and 70 microns in length. The inlet and outlet were also equilateral triangles in cross-section, with dimensions starting at 1 cm per side, and decreasing in size over 1 cm to 70 microns per side. The instrument employed epi-illumination and collection optics (i.e. collection optics from the same side of the sample as excitation optics) with a 410 nm dichroic mirror to excite the sample and collect the fluorescence emission.

The excitation source was a 100-watt stabilized mercury arc lamp with a 30-micron spot size in the most uniform region of the arc. A UG1 filter selected the optimal excitation wavelength for the DAPI of 365 nm from the emission of the mercury arc lamp. The micro-objective had a 1.25 N.A. corresponding to a collection angle of 120 degrees for collection of the fluorescence emission. The DNAnalyzer then used Digital Pulse Processing (DPP) to determine the peak value of the fluorescence emission and nuclear volume from each nucleus.

B. Sample Analysis

Samples of stained nuclei prepared as described in Example I were analyzed as follows. Approximately 50 ul of the TRBC stock suspension was added to each sample as an internal DNA standard. The sample was then analyzed on the DNAnalyzer at a flow rate of 60 to 120 nuclei/second and at least 15,000 events were collected. The data were collected at 8 bits of resolution for both ENV and DNA fluorescence, and presented in an FCS 2.0 standard file format (The Institute of Electrical and Electronics Engineers, Inc; New York N.Y.).

The data were analyzed using Modfit version 5.11 (Verity Software House Inc.; Topsham Me.). The two-parameter graphs were prepared using WinMDI version 2.7. The contour and perspective plots were analyzed in log mode with the interval set at 85%, smooth at 6, and threshold at 0.5. The display resolution was 256×265 for the contour and perspective displays.

Calibration was performed for volume using 4 micron calibration spheres and the known value for trout RBC nuclei of 5 pg of DNA per TRBC nucleus.

C. Determination of NPEs

Normal cells were prepared as described in Example I and measured for nuclear volume (cubic microns) and DNA content (picograms DNA). NPEs were determined in terms of DNA/ENV:

| tissue type | pg DNA | cu. micron | NPE |
|---|---|---|---|
| lymphocyte | 7.75 | 21.3 | 0.364 |
| lymph node | 7.60 | 21.8 | 0.348 |
| breast | 8.14 | 23.6 | 0.345 |
| colon | 7.90 | 22.2 | 0.356 |
| intestine | 7.81 | 21.8 | 0.358 |
| thyroid | 8.29 | 24.3 | 0.341 |

Alternative formulas for NPEs were also determined:

| tissue type | ENV/DNA | DNA²/ENV | (DNA + ENV)/ENV |
|---|---|---|---|
| lymphocyte | 2.75 | 2.82 | 1.364 |
| lymph node | 2.87 | 2.65 | 1.348 |
| breast | 2.90 | 2.81 | 1.345 |
| colon | 2.81 | 2.81 | 1.356 |
| intestine | 2.79 | 2.80 | 1.358 |
| thyroid | 2.93 | 2.83 | 1.341 |

D. Graphical Methods for Determining NPEs

Figure 5A:
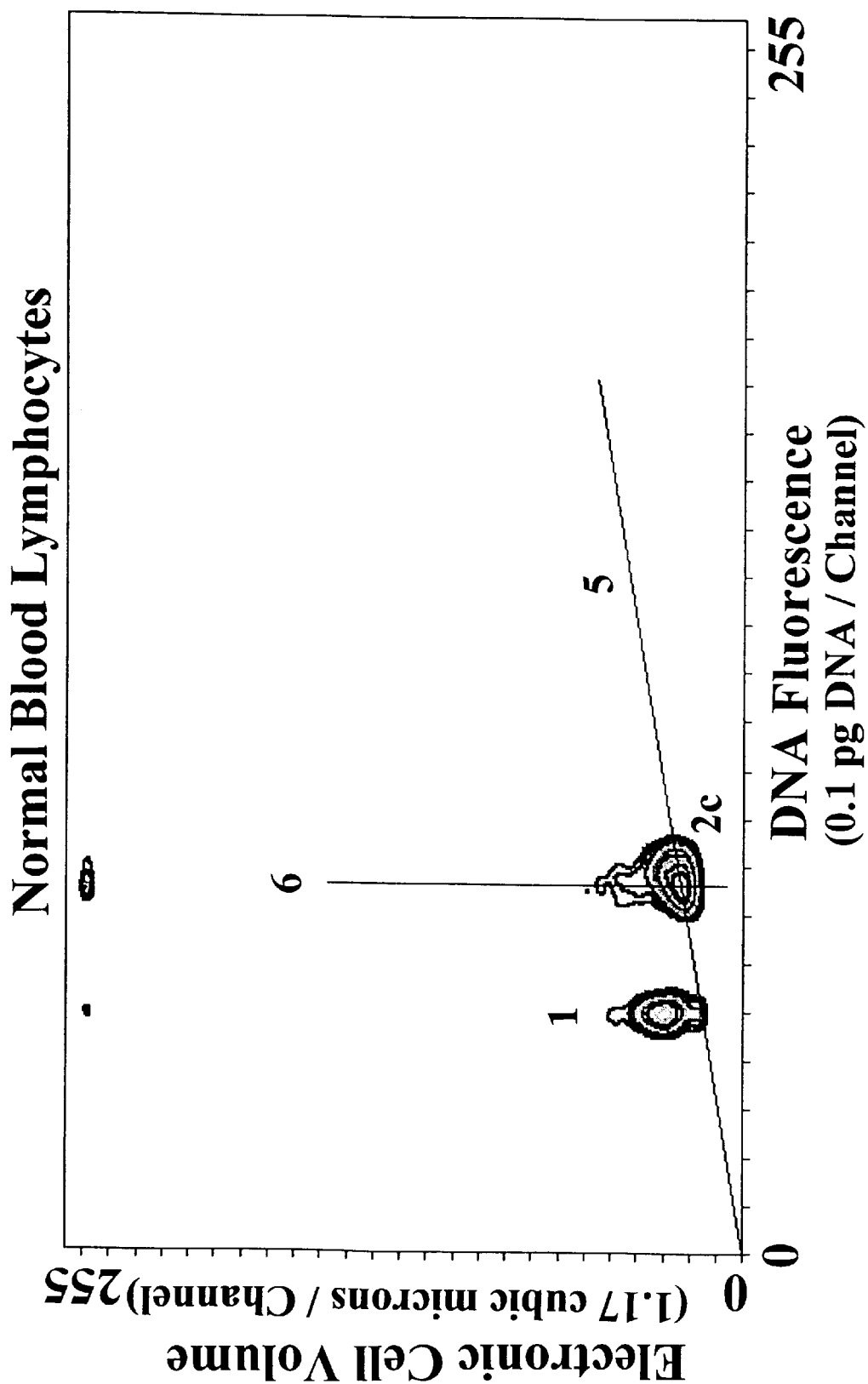
FIGS. 5a to 5c illustrate NPE contours for human lymphocytes in various states: normal lymphocytes (FIG. 5a), leukemic lymphocytes (FIG. 5b), and activated lymphocytes (FIG. 5c).

Examples of NPE contours for normal human tissue are presented in the figures for surface epithelial tissue from mouth (FIG. 1a), intestine (FIG. 1b), thyroid (FIG. 1c), lymph node (FIG. 2a), colon (FIG. 3a) and lymphocytes (FIG. 5a). A perspective view of FIG. 2a is provided as FIG. 2b to emphasize the relative heights of the peaks.

In each of the figures, internal standard TRBC appears as cluster 1. The values for cubic microns and picograms of DNA per channel accompany each of the axes. A line 5 passes through the origin and the $G_0/G_1$ peak 2 and any diploid $G_2+M$ peak 4 visible. An NPE (ENV/DNA) can then determined to be the slope of the line 5. Alternatively, the inverse slope (DNA/ENV) can be used as the NPE.

EXAMPLE III

Using NPEs to Characterize Cells

This example illustrates the use of NPEs to characterize cells, for example by distinguishing among normal and neoplastic cells, and cells in different stages of differentiation and apoptosis.

A. Human Lymph Node Cells

For reference, FIG. 2a shows an NPE contour for cells from normal human lymph node. The $G_0/G_1$, cluster 2 and diploid $G_2+M$ cluster 4 are relatively circular and their centers are aligned on NPE line 5.

In contrast to FIG. 2a, FIG. 2c shows an NPE contour for cells from benign breast tumor. The normal cells 2, 4 have an NPE of about 0.145 (pg DNA/cu. microns), shown as normal NPE line 5. As shown, the shape of the $G_0/G_1$ cluster 2 has stretched vertically by the presence of aneuploid cells 2c. At the upper edge of the 2c cluster, the NPE can be as low as 0.023 (pg DNA/cu. microns). This change in the shape of the cluster is indicative of a neoplastic state. It should be noted that the gradient line 6 is essentially vertical in this figure, expressible as a nearly vertical slope of 1041 (change in volume/change in DNA). Also, the TRBC internal standard 1 is also stretched somewhat as an artifact, due to adhesion of foreign particles to the TRBCs.

FIG. 2d shows an NPE contour for cells from a malignant primary breast tumor. As shown, the $G_0/G_1$ cluster 2 and diploid $G_2+M$ cluster 4 are both elongated by aneuploid cells 2c and 2d. Significantly, the gradient lines 6 are tilted clockwise from the vertical, expressible as a relatively less vertical slope of 9.4. Thus, a change in the slope of the gradient line of a cluster can be indicative of an abnormal condition such as a malignant neoplastic state.

FIG. 2e shows an NPE contour for metastatic cells from the primary breast tumor in FIG. 2d. The two aneuploid clusters 2c and 2d from FIG. 2d are clearly recognizable by the slope of the clusters, gradient slope and NPE slopes in the metastatic aneuploid populations 2c and 2d in FIG. 2e. Thus, a change in the width, breadth or shape of the peak can be a significant indication of an abnormal cell condition such as metastasis. Moreover, FIG. 2e shows that aneuploid population 2d can be clearly discerned from the diploid $G_2+M$ population 4.

Furthermore, in FIG. 2e, the second aneuploid population 2d accounts for 3.4% of the cells, compared to 0.9% of the cells in the diploid $G_2+M$ population 4, showing a high ratio of second aneuploid cells compared to $G_2+M$ cells. Previously, tetraploidy could only be confirmed when the $G_2+M$ population was greater than 15%. Here, this ratio can be observed with $G_2+M$ levels lower than previously known in the field and could previously be observed from a profile of DNA fluorescence alone (see Hankey et al., *Cytometry* 14:472–477 (1993)).

B. Human Colon Cells

Figure 3A:
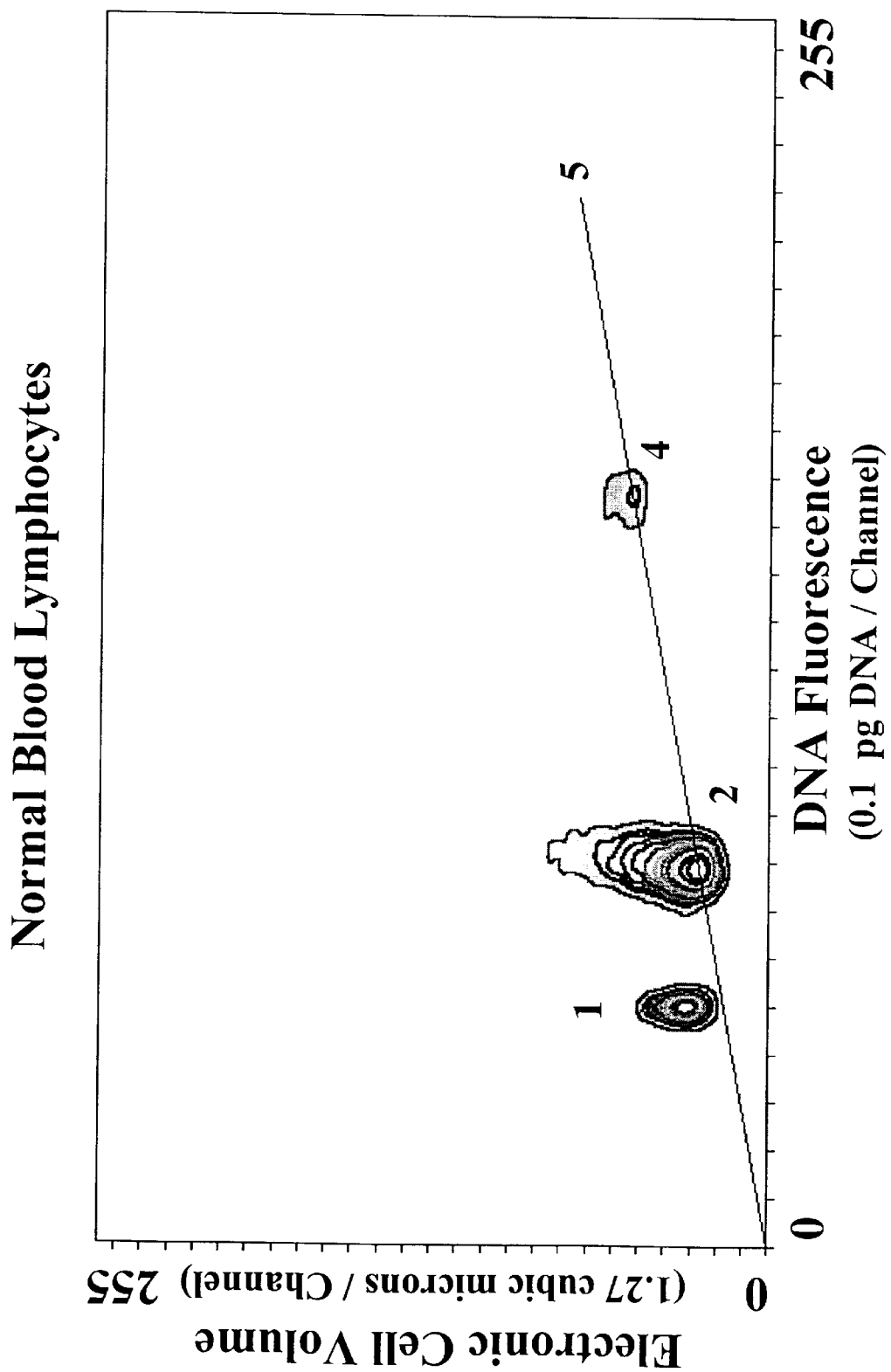
FIGS. 3a to 3c compare NPE contours for cells from human colon in various states: normal colon cells (FIG. 3a), cells from a primary colon tumor (FIG. 3b) and metastatic cells taken from an end point of a surgical resection performed to remove the tumor shown in FIG. 3b (FIG. 3c).

FIG. 3a shows an NPE contour for cells from normal human colon.

Figure 3B:
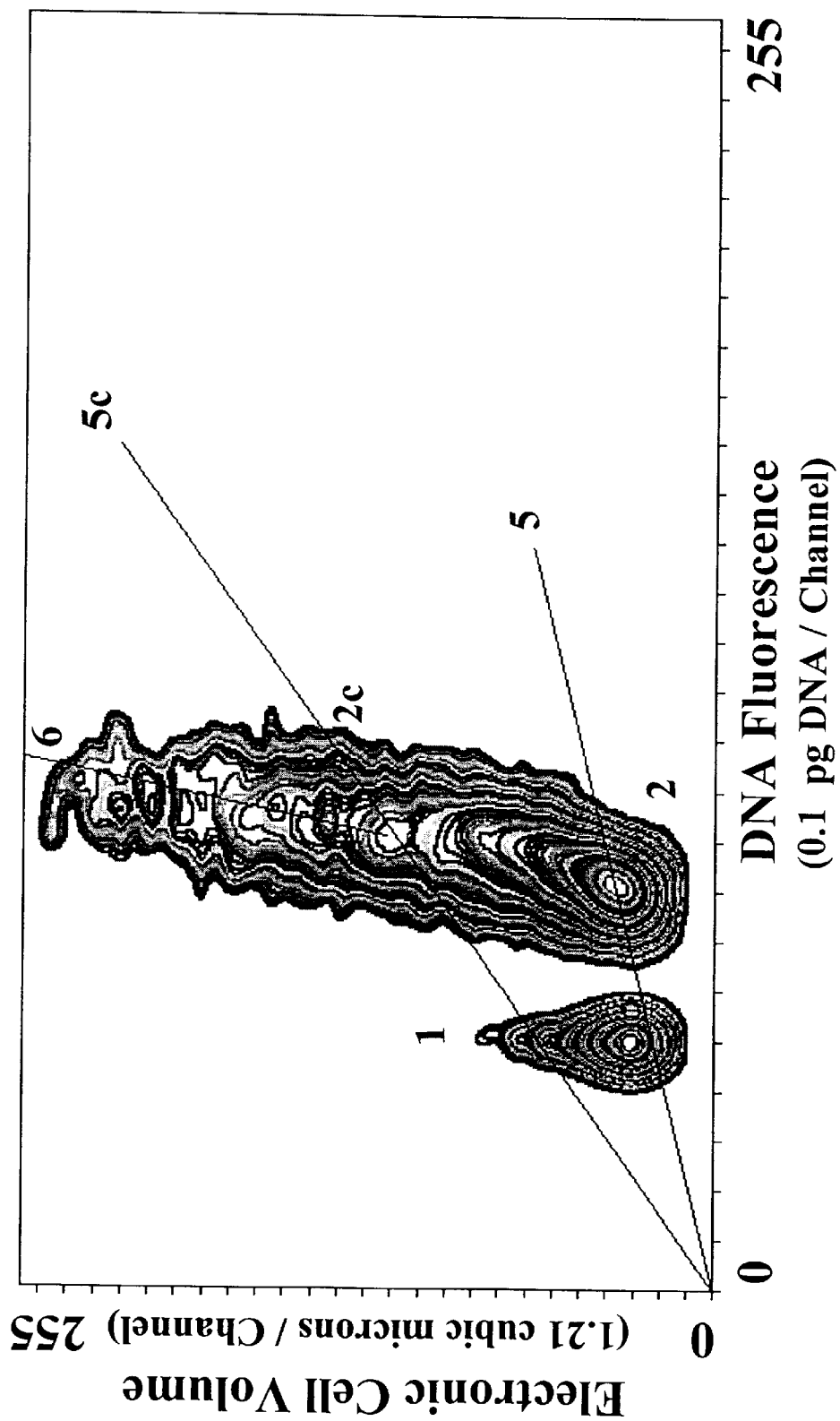
Figure 4C:
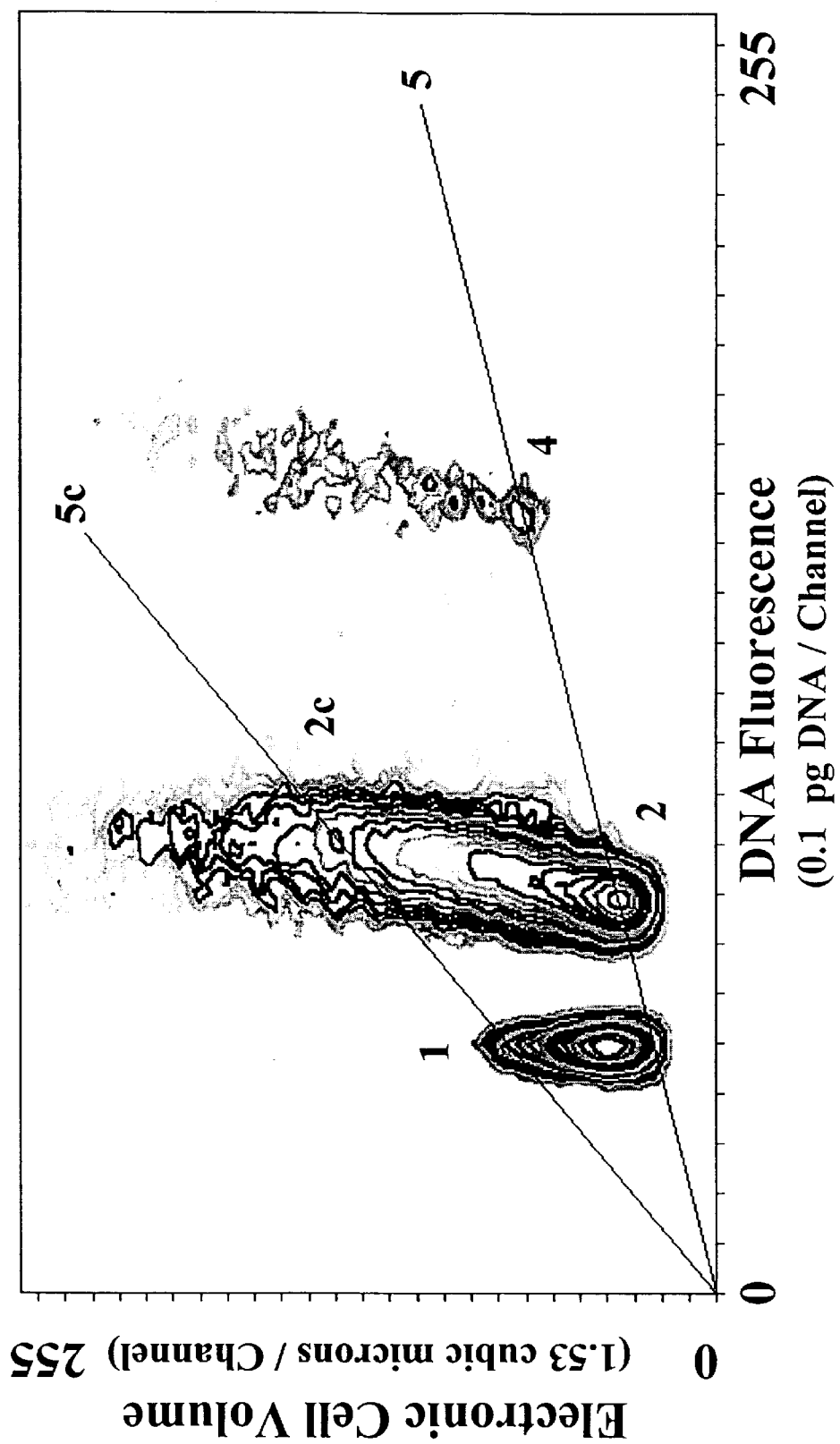
Figure 4D:
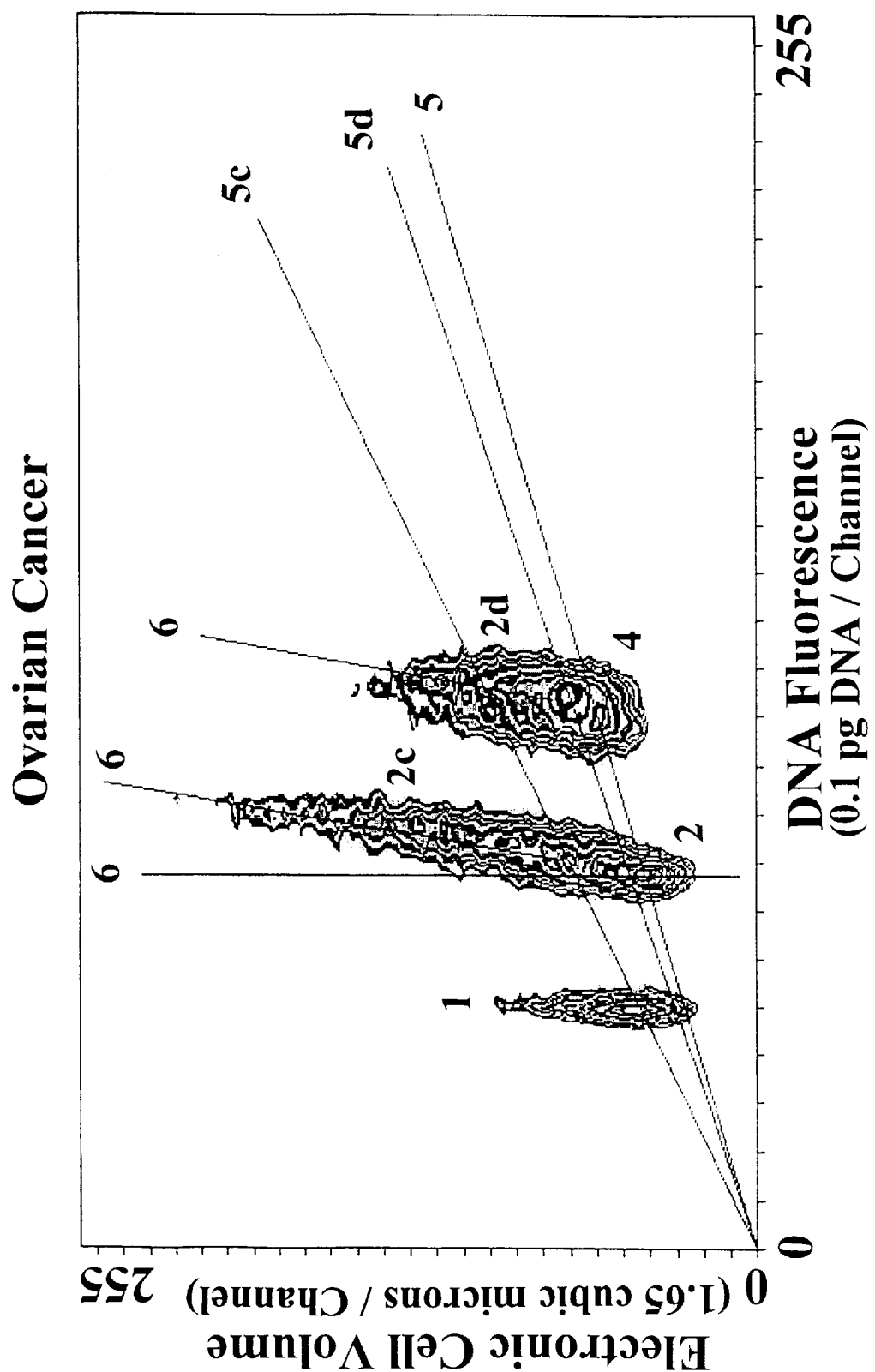

FIG. 3b shows an NPE contour for cells from a primary tumor. Significantly, the $G_0/G_1$ cluster 2 has become elongated by aneuploid cells 2c, and has a tilted gradient line 6. An aneuploid NPE line 5c is shown passing through the cluster of aneuploid cells 2c.

Figure 3C:
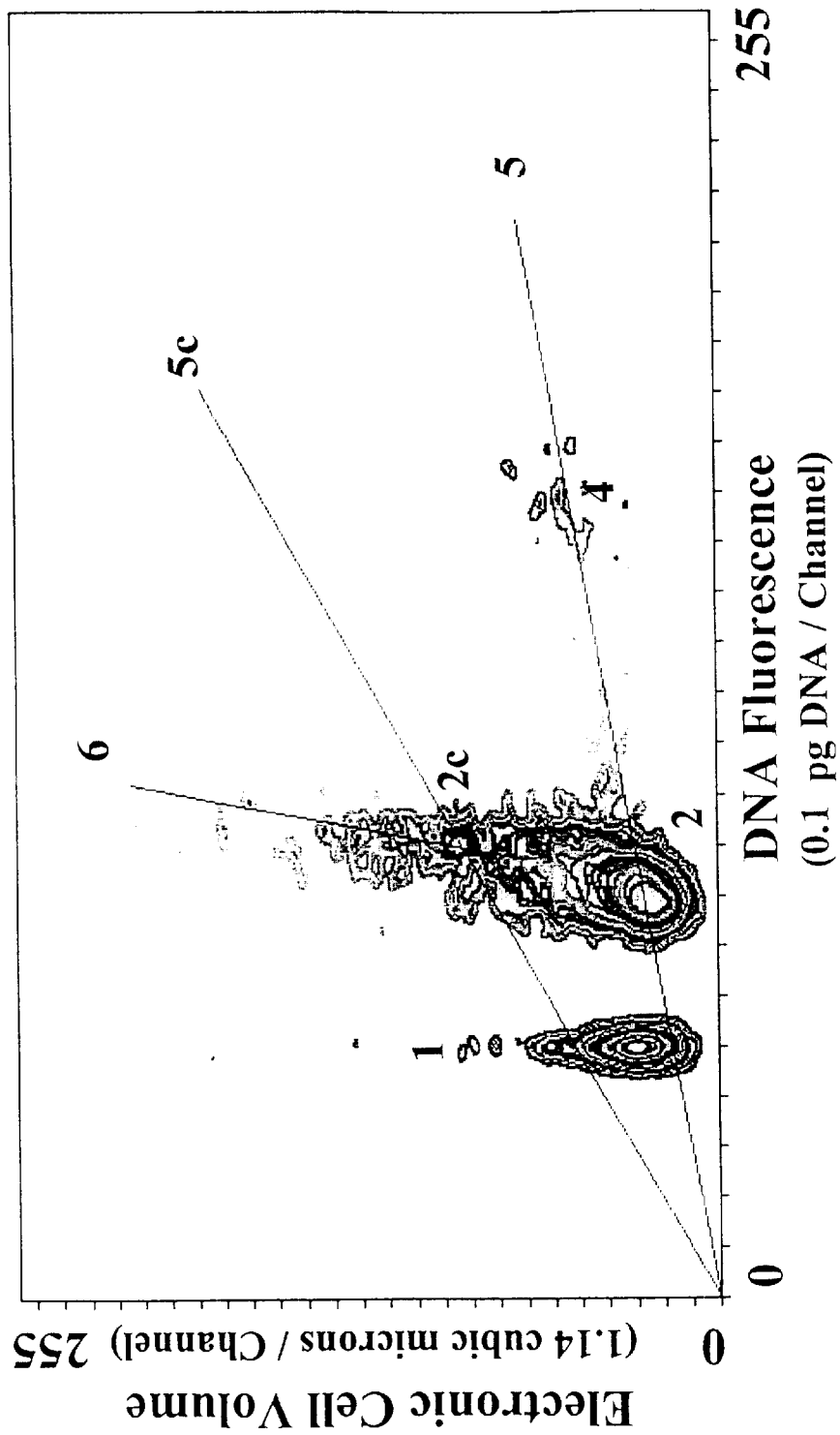

FIG. 3c shows an NPE contour for cells taken from at the end point of resection when surgically removing a metastasizing tumor shown in FIG. 3b. As shown, the aneuploid cells 2c are still present and have a tilted gradient line 6, indicating the resection sample contains metastatic cells.

Figure 4F:
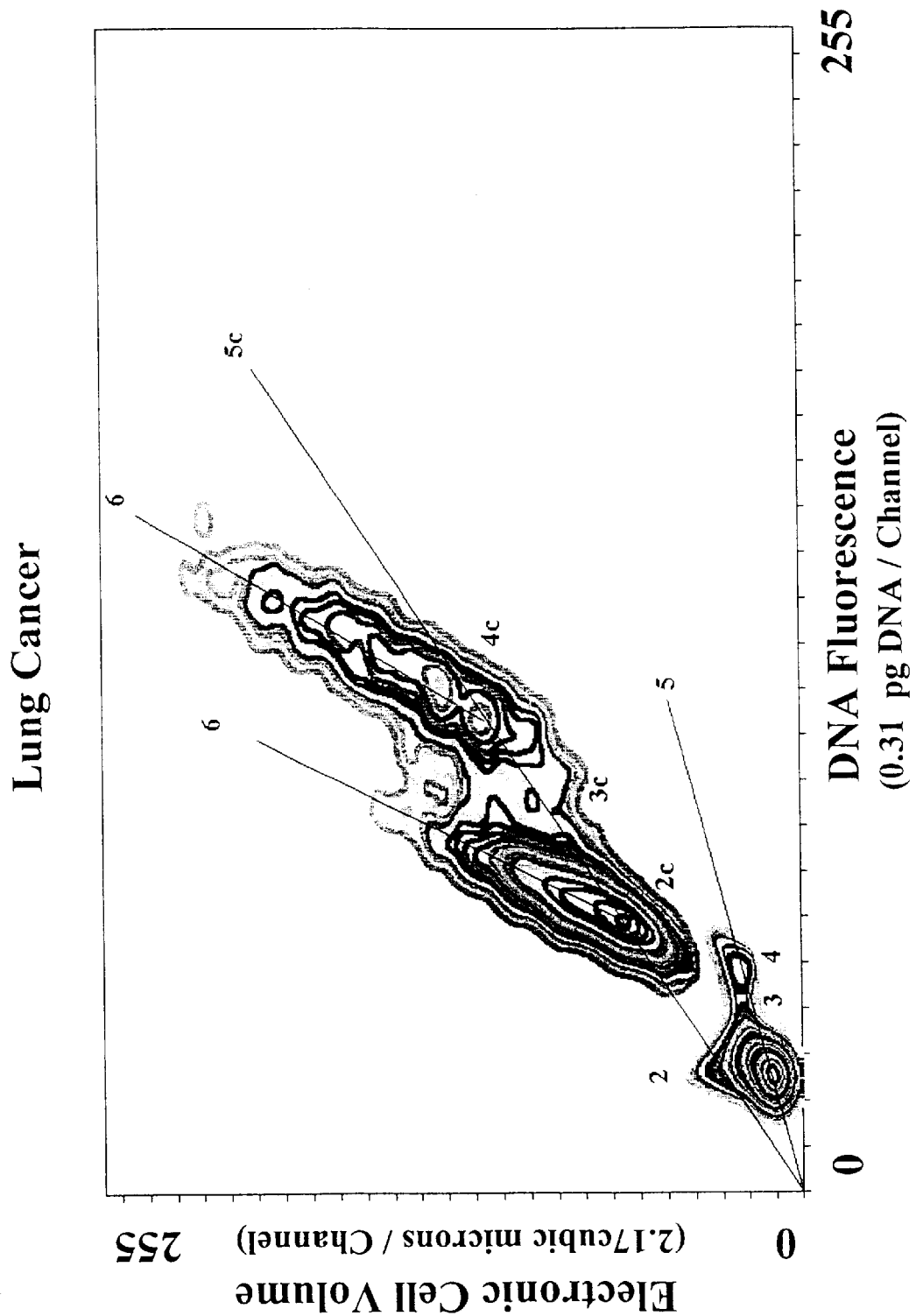

FIGS. 4a to 4f show NPE contours for other ancerous tissue sources: gastric (FIG. 4a and erspective view FIG. 4b), prostate (FIG. 4c), ovarian (FIG. 4d and perspective view FIG. 4e) and lung (FIG. 4f). Notably, FIG. 4f of lung cancer cells-shows a cluster of aneuploid S cells 3c and a cluster of aneuploid $G_2+M$ cells 4c (TRBC standard omitted for scaling reasons), as well as a distinct aneuploid-NPE line 5c passing through 2c, 3c and 4c.

C. Human Lymphocytes

FIG. 5a shows an NPE contour for normal blood lymphocytes. The $G_0/G_1$ cluster 2 is very slightly elongated vertically.

Figure 5B:
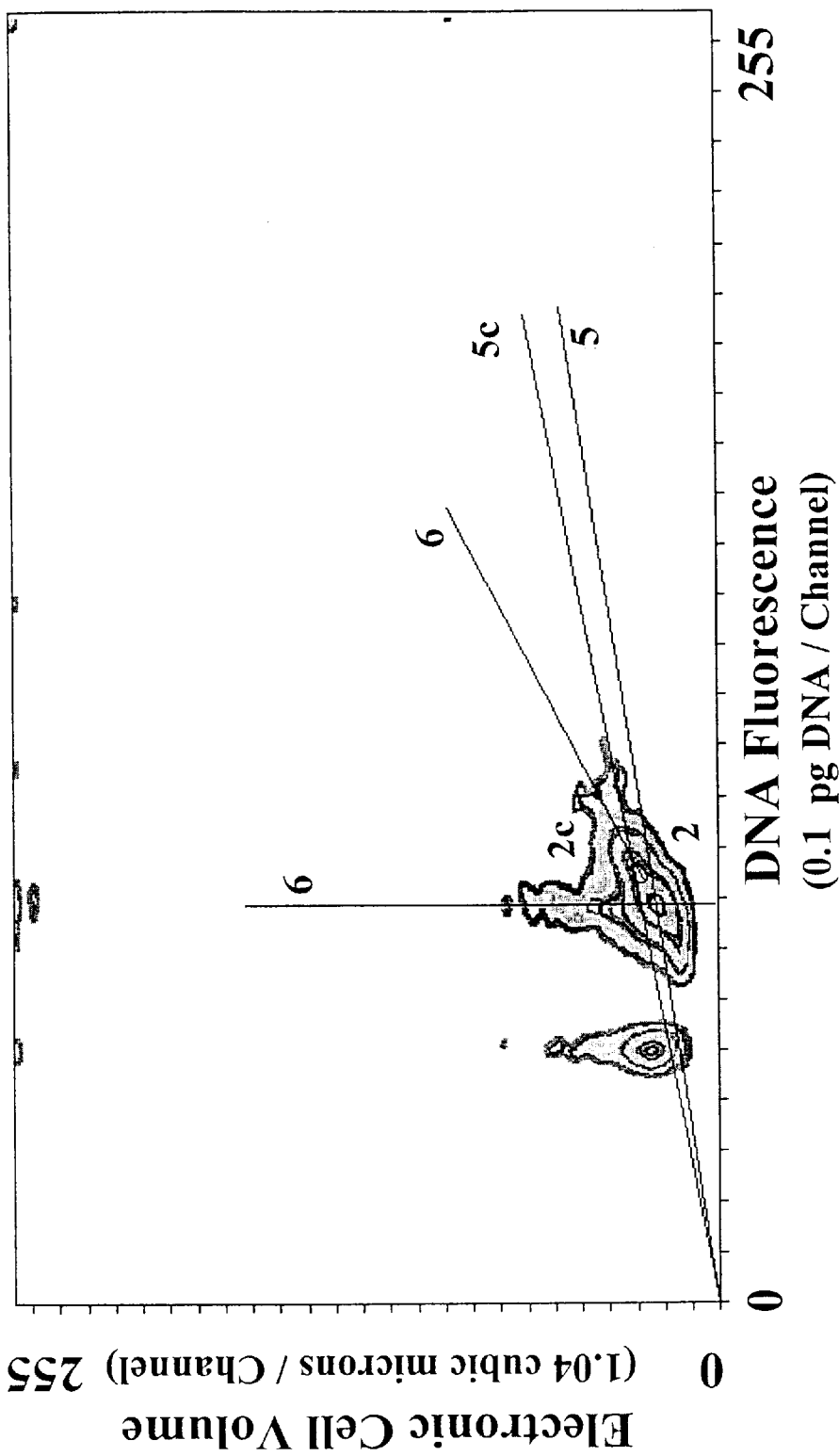

FIG. 5b shows an NPE contour for leukemic lymphocytes. As shown, the presence of aneuploid cells 2c has altered the shape of the $G_0/G_1$ cluster 2, resulting in a tilted gradient line 6 and an NPE 5c for the aneuploid population clearly discernable from the diploid NPE line 5. The NPE contour provides a clear indication that aneuploid cells 2c are present in the sample.

Figure 5C:
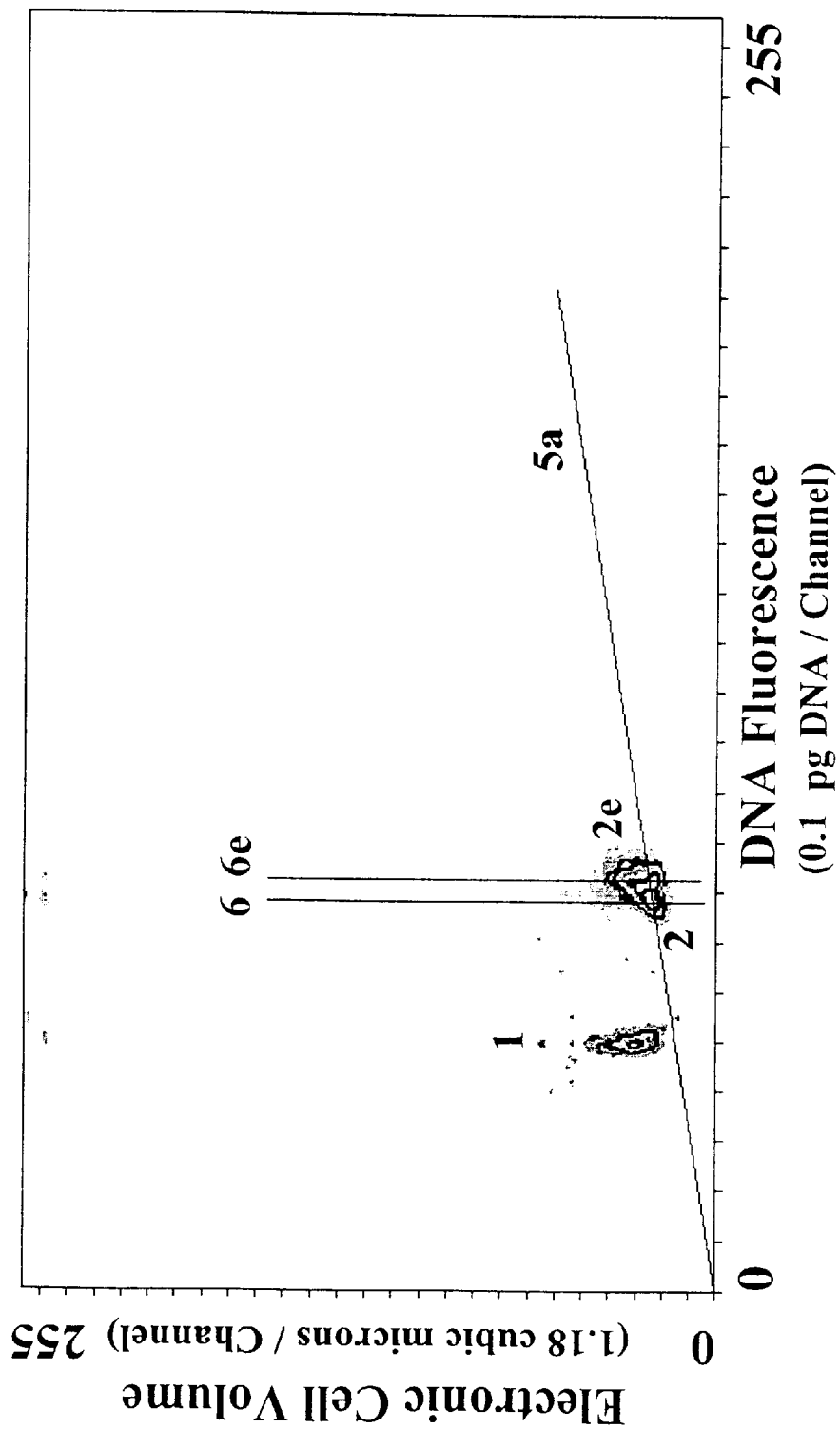

FIG. 5c shows an NPE contour for a cell sample of normal blood containing activated lymphocytes. In addition to the $G_0/G_1$ cluster 2, an additional cluster of activated lymphocytes 2e is discernable, with a distinct vertical gradient line 6e. Thus an NPE contour is useful for detecting cells having a different state of differentiation.

D. Cell Cycle

Figure 6A:
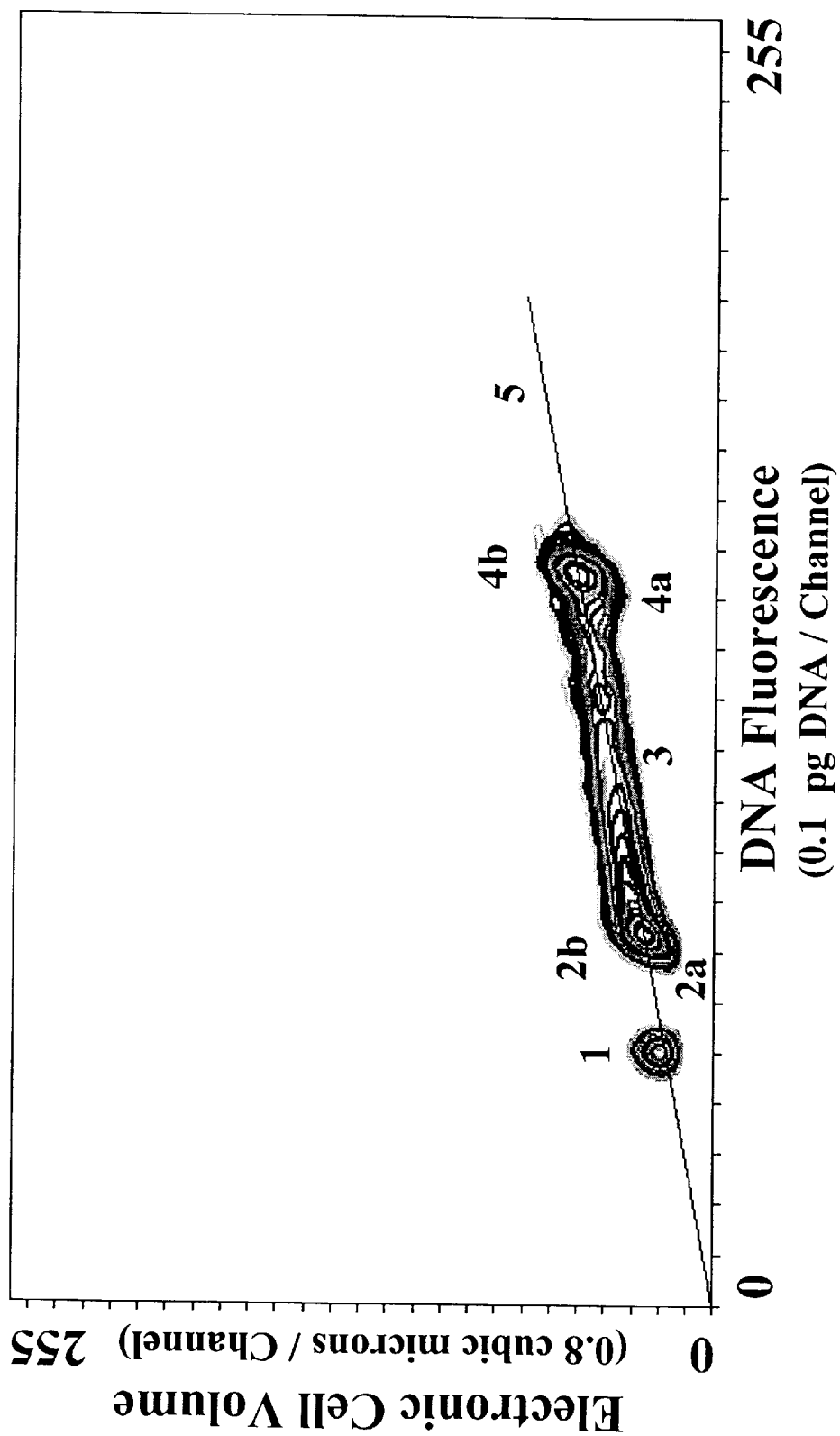
FIG. 6a shows an NPE contour for cells from mouse cell line P388.

The progress of the cell cycle can be traced in FIG. 6a, which shows a contour of datapoints from a sample of a mouse cell line containing cells at various stages of the cell cycle. Cells at $G_0$ phase are shown in cluster 2a. A slight increase in nuclear volume is reflected by the cells in $G_1$ phase in cluster 2b. Once the cells begin replicating their DNA during S phase 3, the values for DNA fluorescence begin to increase until they are double the values for cells in $G_0$ phase, where they remain in $G_2$ phase 4a. Corresponding aneuploid cells in S phase 3c and $G_2+M$ phase 4c are shown in FIG. 4f.

Upon initiating nuclear division, the cells in M phase 4b show a slight increase in nuclear volume. Once nuclear division is complete, the amount of DNA and the nuclear volume are both halved, as shown by the return to $G_0$ phase 2a. Thus, the progress of cells through each stage of the cell cycle is reflected in the clusters identifiable in FIG. 6a. The cell cycle can also be seen in FIGS. 2a and 2b. Remarkably, the clusters remain aligned on the NPE line 5 throughout, demonstrating that the characteristic NPE for the cell line is maintained, even while the nuclei and cells are dividing.

E. Apoptotic Cells

Figure 6B:
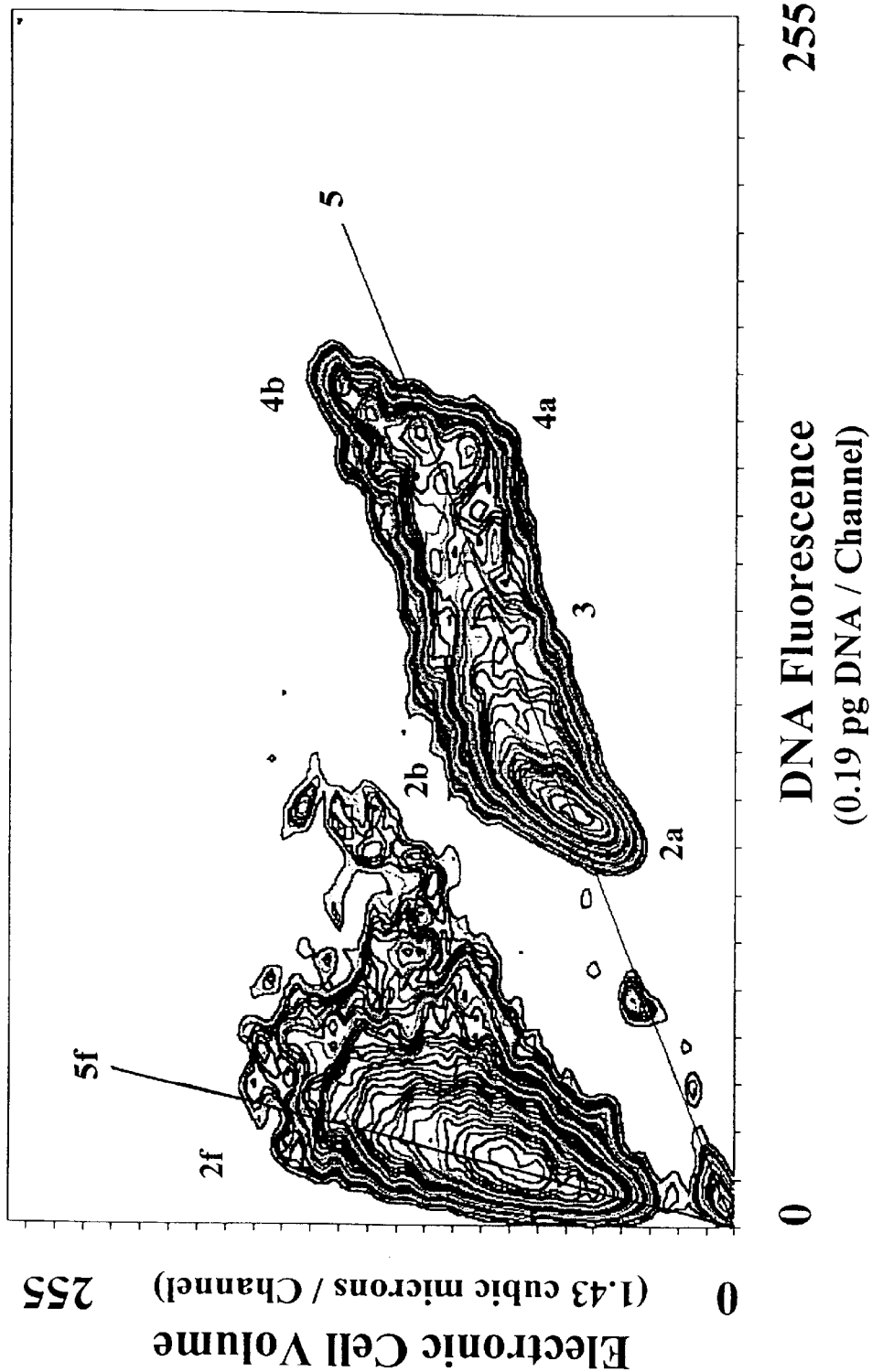
FIG. 6b shows NPE contours for normal and apoptotic cells from a WEHI-231 murine B lymphoma cell line (FIG. 6b and perspective view 6c).

WEHI cells from a WEHI-231 murine B lymphoma cell line (Lombardi Cancer Institute; Wash. D.C.) were obtained untreated or treated with an apoptotic agent. As shown in FIG. 6b, the NPE contour for nonapoptotic cells contains cells in various stages of the cell cycle, as discussed above (clusters 2a, 2b, 3, 4a, 4b). The apoptotic cells are in a distinct cluster 2f, with a different NPE line 5f. The separation between the nonapoptotic and apoptotic cells is highlighted in perspective view FIG. 6b (the origin is in the distant upper right corner). It can be observed that the volume of the nucleus remains relatively constant whether apoptotic or not, but the measured DNA decreases during apoptosis, whether due to decrease in DNA content or in DNA staining. This suggests that the volume of the nucleus during apoptosis is not maintained by the DNA content, but by other components, such as the nuclear matrix.

Although the invention has been illustrated by the examples above, it should be understood that various modifications can be made without departing from the spirit of the invention. Accordingly, the invention is limited only by the following claims.

I claim:

1. A method for determining the packing efficiency (NPE) of a procaryotic cell, comprising the steps of
   (a) measuring a biochemical component (BC) of the cell;
   (b) measuring a spatial displacement of the cell (SDN); and
   (c) determining a packing efficiency (NPE) by correlating the values of BC and SDN.

2. A method for determining the packing efficiency (NPE) of a virus, comprising the steps of
   (a) measuring a biochemical component (BC) of the virus;
   (b) measuring a spatial displacement of the virus (SDN); and
   (c) determining a packing efficiency (NPE) by correlating the values of BC and SDN.

3. A method for determining the nuclear packing efficiency (NPE) of a cell, comprising the steps of
   (a) measuring a biochemical component (BC) of the nucleus of a cell;
   (b) measuring a spatial displacement of the nucleus (SDN) of the cell using electronic cell volume (ECV); and
   (c) determining a nuclear packing efficiency (NPE) by correlating the values of BC and SDN.

4. A method for determining an NPE for a population of cells, comprising the steps of
   (a) for a representative number of cells in the population:
      (1) measuring a biochemical component (BC) of the nucleus of a cell;
      (2) measuring a spatial displacement of the nucleus (SDN) of the cell using electronic cell volume (ECV); and
      (3) determining a datapoint for BC and SDN on separate axes for BC and SDN;
   (b) identifying at least one cluster of the datapoints; and
   (c) determining an NPE according to a preselected geometric parameter of the cluster of datapoints.

5. A method for determining the nuclear packing efficiency (NPE) of a cell, comprising the steps of
   (a) measuring a biochemical component (BC) of the nucleus of a cell;
   (b) measuring a spatial displacement of the nucleus (SDN) of the cell using nuclear envelope volume; and
   (c) determining a nuclear packing efficiency (NPE) by correlating the values of BC and SDN.

6. A method for determining an NPE for a population of cells, comprising the steps of
   (a) for a representative number of cells in the population:
      (1) measuring a biochemical component (BC) of the nucleus of a cell;
      (2) measuring a spatial displacement of the nucleus (SDN) of the cell using nuclear envelope volume; and
      (3) determining a datapoint for BC and SDN on separate axes for BC and SDN;
   (b) identifying at least one cluster of the datapoints; and
   (c) determining an NPE according to a preselected geometric parameter of the cluster of datapoints.

7. The method of claim 3, wherein the ECV is adjusted using flow cytometry time-of-flight (TOF).

8. The method of claim 4, wherein the ECV is adjusted using flow cytometry time-of-flight (TOF).

9. The method of claim 3, 5, 4, 6, 7 or 8, wherein the SDN is the volume of a eucaryotic nucleus.

10. The method of claim 1, 2, 3, 5, 4, 6, 7 or 8, wherein the BC includes nucleic acid.

11. The method of claim 10, wherein the nucleic acid is DNA.

12. The method of claim 11, wherein the DNA is easured by fluorescence.

13. The method of claim 10, wherein the nucleic acid is RNA.

14. The method of claim 1, 2, 3, 5, 4, 6, 7, or 8, wherein the BC includes nuclear water.

15. The method of claim 1, 2, 3, 5, 7, or 8, wherein step (c) is performed according to the formula $$NPE = k_1(BC)^a/(SDN)^b + k_2(BC)^c + k_3(SDN)^d + k_4;$$

wherein $k_1$, $k_2$, $k_3$, $k_4$, a, b, c and d are preselected constants and $k_1$ is not zero.

16. The method of claim 15, wherein $k_1$ is positive.

17. The method of claim 15, wherein $k_2$ is zero.

18. The method of claim 15, wherein $k_4$ is zero.

19. The method of claim 15, wherein $k_1=1$, a=1 and b=1, whereby NPE=BC/SDN.

20. The method of claim 1, 2, 3, 5, 7 or 8, wherein step (c) is performed by performing the steps of
   (c1) determining a datapoint for BC and SDN on separate axes for BC and SDN; and
   (c2) determining NPE as the slope of a line passing through the datapoint and the origin of the axes.

21. The method of claim 4 or 6, wherein the geometric parameter is the slope of a substantially linear curve passing through the local maxima of at least one cluster and through the origin of the BC and SDN axes.

22. The method of claim 4 or 6, wherein the geometric parameter is the slope of the gradient line of the cluster of datapoints.

23. The method of claim 4 or 6 wherein the geometric parameter is selected from the group consisting of eccentricity, maximum range of the major axis, maximum range of the minor axis, standard deviation of the major axis, standard deviation of the minor axis, slope of a line orthogonal to the gradient line, and perimeter.

24. The method of claim 1, 2, 3, 5, 4, 6, 7 or 8, wherein the BC includes protein.

25. The method of claim 1, 2, 3, 5, 4, 6, 7 or 8, wherein the BC includes lipid.

* * * * *

UNITED STATES PATENT AND TRADEMARK OFFICE
CERTIFICATE OF CORRECTION

PATENT NO. : 6,587,792 B1
DATED : July 1, 2003
INVENTOR(S) : Thomas

It is certified that error appears in the above-identified patent and that said Letters Patent is hereby corrected as shown below:

<u>Column 16,</u>
Line 27, please delete "easured", replace therefor with -- measured --.

Signed and Sealed this

Thirteenth Day of July, 2004

JON W. DUDAS
*Acting Director of the United States Patent and Trademark Office*